(12) United States Patent
Holland et al.

(10) Patent No.: US 6,413,730 B1
(45) Date of Patent: Jul. 2, 2002

(54) METHOD FOR IDENTIFYING COMPOUNDS THAT INHIBIT OR ENHANCE ACTIVATION OF A TRANSMEMBRANE LIGAND FOR A RECEPTOR TYROSINE KINASE

(75) Inventors: Sacha Holland; Geraldine Mbamalu; Tony Pawson, all of Toronto (CA)

(73) Assignee: Mount Sinai Hospital Corporation, Toronto (CA)

(*) Notice: Subject to any disclaimer, the term of this patent is extended or adjusted under 35 U.S.C. 154(b) by 0 days.

(21) Appl. No.: 09/214,631
(22) PCT Filed: Jul. 4, 1997
(86) PCT No.: PCT/CA97/00473
§ 371 (c)(1), (2), (4) Date: Mar. 12, 1999
(87) PCT Pub. No.: WO98/01548
PCT Pub. Date: Jan. 15, 1998

Related U.S. Application Data

(60) Provisional application No. 60/021,272, filed on Jul. 5, 1996.

(51) Int. Cl.$^7$ ............... G01N 33/53; G01N 33/567
(52) U.S. Cl. ............... 435/7.6; 435/7.1; 435/7.21; 435/7.8
(58) Field of Search ............... 435/7.1, 7.2, 7.21, 435/7.6, 7.8

(56) References Cited

U.S. PATENT DOCUMENTS

| | | | |
|---|---|---|---|
| 5,350,836 A | * | 9/1994 | Kopchick et al. |
| 5,457,048 A | | 10/1995 | Pasquale et al. |
| 5,681,714 A | * | 10/1997 | Breitman et al. ......... 435/69.1 |

FOREIGN PATENT DOCUMENTS

| | | |
|---|---|---|
| WO | PCT/AU92/00294 | 6/1992 |
| WO | WO 94/11384 | 5/1994 |
| WO | PCT/US94/13214 | 11/1994 |
| WO | WO 95/06065 | 3/1995 |
| WO | PCT/CA95/00254 | 4/1995 |
| WO | PCT/US95/04208 | 4/1995 |
| WO | PCT/US 95/04681 | 4/1995 |
| WO | WO 96/01839 | 1/1996 |
| WO | PCT/US96/02673 | 2/1996 |
| WO | WO 97/14966 | 4/1997 |

OTHER PUBLICATIONS

Vukicevic et al. PNAS USA 93:9021–9026, 1996.*
Massague J. Cell 49:437–8, 1987.*
Pilbeam et al. Bone 14:717–720, 1993.*
Skolnick et al. Trends in Biotech. 18:34–39, 2000.*
Kenny D, et al. The receptor tyrosine kinase QEK5 mRNA is expressed in a gradient within the neural retina and the tectum. Developmental Biology. vol. 172, pp. 708–716, 1995.*
Letwin K et al. Novel protein–tyrosine kinase cDNAs related to fps/fes and eph cloned using anti–tyrosinephosphatase antibody. Oncogene. vol. 6, pp. 621–627, 1988.*
Bennett BD, et al. Cloning and characterization of Htk, a novel transmembrane tyrosine kinase of the Eph subfamily. J. Biol. Chem. vol. 269, pp. 14211–14218, 1994.*
Wicks IP, et al. Molecular cloning of HEK, the gene encoding a receptor tyrosine kinase expressed by human lymphoid tumor cell line. Proc. Natl. Acad. Sci. USA. vol. 1611–1615, 1992.*
Bork P. Genome Research 10:398–400, 2000.*
Doerks et al. Trends in Genetics 14:248–250, 1998.*
Smith et al. Nature Biotechnology 15:1222–1223, 1997.*
Brenner SE. Trends in Genetics 15:132–133, 1999.*
Bork et al. Trends in Genetics 12:425–427, 1996.*
Gale, N.W. et al., "EPH Receptors and Ligands Comprise Two Major Specificity Subclasses and Are Reciprocally Compartmentalized during Embryogenesis", Neuron, vol. 17, pp. 9–17(Jul. 1996).
Holland, S.J. et al., "Bidirectional Signalling Through the EPH–Family Receptor Nuk and Its Transmembrane Ligands", Nature, vol. 383, pp. 722–725 (Oct. 24, 1996).
Wang, X et al., "Multiple Ephrins Control Cell Organization in C. elegans Using Kinase–Dependent and –Independent Functions of the VAB–1 Eph Receptor", Molecular Cell, vol. 4, pp. 903–913 (Dec. 1999).
Hirai et al., Science 238:1717–1720, 1987.
Letwin et al., Oncogene 3:621–627, 1988.
Lindberg et al., Mol. Cell. Biol. 10:6316–6324, 1990.
Lhotak et al., Mol. Cell. Biol. 11:2496–2502, 1991.
Toyoshima, H. et al., Proc. Natl. Acad. Sci. USA, vol. 90, pp. 5404–5408, 1993
Vetter , M. and Michael Bisho, J., Current Biology, vol. 5, pp. 168–178, 1995.
Chan and Watt, Oncogene 6:1057–1061, 1991.
Pasquale, Cell Regulation 2:523–534, 1991.
Sajjadi et al., New Biologist 3:769–778, 1991.
Wicks et al., PNAS 89:1611–1615, 1992.
Gilardi–Hebenstreit et al., Oncogene 7:2499–2506, 1992.
Bohme et al., Oncogene 8:2857–2862, 1993.
Sajjadi and Pasquale, Oncogene 8:1801–1813, 1993.
Hynes, R.O. and Landers, A.D., Cell 68, 303–322, 1992.
Dodd, J. and Jessell, T.M., Science, 262, 692–699, 1988.
Jessell, T.M., Neuron, 1, 3–13, 1988.

(List continued on next page.)

Primary Examiner—Lorraine Spector
Assistant Examiner—Robert S. Landsman
(74) Attorney, Agent, or Firm—Merchant & Gould P.C.

(57) ABSTRACT

A method of modulating the biological activity of a transmembrane ligand for an Elk-related receptor tyrosine kinase in a cell expressing the transmembrane ligand, comprising forming a complex between a purified and isolated oligomerized Elk-related receptor tyrosine kinase, or an isoform or an extracellular domain of the kinase, and a transmembrane ligand expressed on the cell, thereby affecting a pathway in the cell which is regulated by the transmembrane ligand.

5 Claims, 12 Drawing Sheets

OTHER PUBLICATIONS

Furley et al., Cell 61, 157–170, 1990.
Burns et al., Neuron, 7, 209–220, 1991.
Bastiani et al., Cell 48:745–755, 1987.
Elkins et al., Cell 60:565–575, 1990.
Grenningloh et al., Cold Spring Harb. Symp. Quant. Biol. 55, 327–340, 1991.
Nose et al., Cell 70:553–567, 1992.
Hatta et al., Dev. Biol. 120:215–227, 1987.
Takeichi, Development 102:639–655, 1988.
Takeichi, Annu. Rev. Biochem. 59:237–252, 1990.
Takeichi, Science 251:1451–1455, 1991.
Edelman, Biochemistry 27:3533–3543, 1988.
Grumet, Curr. Opin. Neurobiol. 1:370–376, 1991.
Detrick et al., Neuron 4:493–506, 1990.
Fujimori et al., Development 110:97–104, 1990.
Goodman and Shatz, Cell 72:77–98, 1993.
Tessier–Lavigne, 1995, Cell 82:345–348.
Drescher et al., 1995 Cell 82:359–370.
Gertler et al., Cell 58:103–113, 1989.
Henkemeyer et al., Cell 63:949–960, 1990.
Tian et al., Cell 67:675–685, 1991.
Yang et al., Cell 67:661–673, 1991.
van der Geer et al., 1994, Annu. Rev. Cell. Biol. 10:251–237.
Lindberg and Hunter, 1990, Mol. Cell. Biol. 10:6316–6324.
Maisonpierre et al., 1993, Oncogene, 8:3277–3288.
Andres, A.C. et al., Oncogene, 9(5):1461–1467, May 1994.
Fox, et al., 1995, Oncogene, 10, 897–905.
Williams and Barclay, Ann. Rev. Immunol. 6:381–405, 1988.
Nieto, et al., Development 116:1137–1150, 1992.
Koch, C.A. et al., 1989, Mol. Cell. Biol. 9, 4131–4140.
Ben–David et al., EMBO 10:317–325, 1991.
Henkemeyer et al., 1994, Oncogene 9:1001–1014.
Holzman et al., 1990, Mol. Cell Biol. 19:5830–5838.
Bartley et al., 1994, Nature 368:558–560.
Beckman et al., 1994, EMBO J. 13:3757–3762.
Davis et al., 1994, Science 266, 816–819.
Fletcher et al., Oncogene 9:3241–3247, 1994.
Shao et al., 1994, J. Biol. Chem. 269:26606–26609.
Cheng and Flanagan, 1994, Cell, 79:157–168.
Kozlosky et al., 1995, Oncogene 10:299–306.
Brambilla et al., 1995, EMBO J. 14:3116–3126.
Lai and Lemke, Neuron 6:691–704, 1991.
Rakie, P., in "The Cell in Contact", ed. G.M. Edelman and J–P Thiery, Wiley & Sons, 1985, Chapter 4.
S.E. Fraser & V. Bayer, in "The Cell in Contact", ed. G.M. Edelman and J–P Thiery, Wiley & Sons, 1985 Chapter 5.
G.E. Edelman, in "The Cell in Contact", ed. G.M. Edelman and J–P Thiery, Wiley & Sons, 1985, Chapter 7.
J–P Thiery et al., in "The Cell in Contact", ed. G.M. Edelman and J–P Thiery, Wiley & Sons, 1985, Chapter 8.

* cited by examiner

FIG. 1A

```
11 hElk-L    LRKRHRKHTQQRAAAALSLS...TLASPKGGS.GTAGTEPS    297
12 hHtk-L    YRRRHRKHSPQHTTTLSLS...TLATPKRSG.NNNGSEPS    287
13 hElk-L3   RRRRAKPSESRHPGPGSFGRGGSLGLGGGGGMGPREAEPG    291 hElk-L    DIIIPLR...TTENNYCPHYEKVSGDYGHPVYIVQEMPPQ    334
   hHtk-L    DIIIPLR...TADSVFCPHYEKVSGDYGHPVYIVQEMPPQ    324
   hElk-L3   ELGIALRGGGAADPPFCPHYEKVSGDYGHPVYIVQDGPPQ    331
                               *       *    * hElk-L    SPANIYYKV    343
   hHtk-L    SPANIYYKV    333
   hElk-L3   SPPNIYYKV    340
               **
```

FIG. 5A

```
                CCGGGGGGTG GGCGACTTTG GGGGAGTTGG TGCCCCGCCC CCCAGGCCTT GGCGGGGTC  59

ATG GGG CCC CCC CAT TCT GGG CCG GGG GGC GTG CGA GTC GGG GCC CTG  107
 M   G   P   P   H   S   G   P   G   G   V   R   V   G   A   L   16

CTG CTG CTG GGG GTT TTG GGG CTG GTG TCT GGG CTC AGC CTG GAG CCT  155
 L   L   L   G   V   L   G   L   V   S   G   L   S   L   E   P   32

GTC TAC TGG AAC TCG GCG AAT AAG AGG TTC CAG GCA GAG GGT GGT TAT  203
 V   Y   W   N   S   A   N   K   R   F   Q   A   E   G   G   Y   48

GTG CTG TAC CCT CAG ATC GGG GAC CGG CTA GAC CTG CTC TGC CCC CGG  251
...  ...  ...  ...  ...  ...  ...  ...  ..T  ..A  ..T  ...  ...  ...  ...  ...
 V   L   Y   P   Q   I   G   D   R   L   D   L   L   C   P   R   64

GCC CGG CCT CCT GGC CCT CAC TCC TCT CCT AAT TAT GAG TTC TAC AAG  299
...  ...  ...  ...  ...  ..C  ...  ...  ...  .G.  ...  ...  ...  ...  ..A
 A   R   P   P   G   P   H   S   S   P   N   Y   E   F   Y   K   80

CTG TAC CTG GTA GGG GGT GCT CAG GGC CGG CGC TGT GAG GCA CCC CCT  347
...  ...  ...  ...  ..C  ...  ..T  ...  ..T  ...  ...  ...  ...  ...  ...
 L   Y   L   V   G   A   Q   G   R   R   C   E   A   P   P   96

GCC CCA AAC CTC CTT CTC ACT TGT GAT CGC CCA GAC CTG GAT CTC CGC  395
...  ..T  ...  ...  ..A  ...  ..C  ..G  ...  ...  ...  ..C  ...  ...
 A   P   N   L   L   L   T   C   D   R   P   D   L   D   L   R   112

TTC ACC ATC AAG TTC CAG GAG TAT AGC CCT AAT CTC TGG GGC CAC GAG  443
...  ...  ...  ...  ..A  ..C  ...  ...  ..C  ...  ...  ...  ...  ...
 F   T   I   K   F   Q   E   Y   S   P   N   L   W   G   H   E   128

TTC CGC TCG CAC CAC GAT TAC TAC ATC ATT GCC ACA TCG GAT GGG ACC  491
...  A.A  ..C  ...  ...  ...  ...  ..A  ...  ...  ..A  ...  ...  ...
 F   R   S   H   H   D   Y   Y   I   I   A   T   S   D   G   T   144

CGG GAG GGC CTG GAG AGC CTG CAG GGA GGT GTG TGC CTA ACC AGA GGC  539
...  ..A  ...  ...  ...  ..T  ...  ...  ...  ...  ...  ...  ...  ...
 R   E   G   L   E   S   L   Q   G   G   V   C   L   T   R   G   160

ATG AAG GTG CTT CTC CAA GTG GGA CAA AGT CCC CGA GGA GGG GCT GTC  587
...  ...  ...  ..G  .G.  ...  ...  ...  ...  ...  ...  ..A  ...  ..A
 M   K   V   L   L  Q/R  V   G   Q   S   P   R   G   A   V   176

CCC CGA AAA CCT GTG TCT GAA ATG CCC ATG GAA AGA GAC CGA GGG GCA  635
...  ...  ...  ...  ...  ...  ...  ..G  ...  ...  ...  ...  ...  ...
 P   R   K   P   V   S   E   M   P   M   E   R   D   R   G   A   192

GCC CAC AGC CTG GAG CCT GGG AAG GAG AAC CTG CCA GGT GAC CCC ACC  683
 A   H   S   L   E   P   G   K   E   N   L   P   G   D   P   T   208

AGC AAT GCA ACC TCC CGG GGT GCT GAA GGC CCC CTG CCC CCT CCC AGC  731
 S   N   A   T   S   R   G   A   E   G   P   L   P   P   P   S   224
                          Transmembrane Domain
ATG CCT GCA GTG GCT GGG GCA GCA GGG GGG CTG GCG CTG CTC TTG CTG  779
 M   P   A   V   A   G   A   A   G   G   L   A   L   L   L   L   240

GGC GTG GCA GGG GCT GGG GGT GCC ATG TGT TGG CGG AGA CGG CGG GCC  827
 G   V   A   G   A   G   G   A   M   C   W   R   R   R   R   A   256

AAG CCT TCG GAG AGT CGC CAC CCT GGT CCT GGC TCC TTC GGG AGG GGA  875
 K   P   S   E   S   R   H   P   G   P   G   S   F   G   R   G   272

GGG TCT CTG GGC CTG GGG GGT GGA GGT GGG ATG GGA CCT CGG GAG GCT  923
 G   S   L   G   L   G   G   G   G   M   G   P   R   E   A   288

GAG CCT GGG GAG CTA GGG ATA GCT CTG CGG GGT GGC GGG GCT GCA GAT  971
 E   P   G   E   L   G   I   A   L   R   G   G   G   A   A   D   304

CCC CCC TTC TGC CCC CAC TAT GAG AAG GTG AGT GGT GAC TAT GGG CAT  1019
 P   P   F   C   P   H   Y   E   K   V   S   G   D   Y   G   H   320

CCT GTG TAT ATC GTG CAG GAT GGG CCC CCC CAG AGC CCT CCA AAC ATC  1067
 P   V   Y   I   V   Q   D   G   P   P   Q   S   P   P   N   I   336

TAC TAC AAG GTA TGA GGGCTCCT CTCACGTGGC TATCCTGAAT CCAGCCCTTC    1120
 Y   Y   K   V   *                                                340
```

FIG. 5C

| Percent Similarity Among Ligands | | | | | | | |
|---|---|---|---|---|---|---|---|
| TM Ligands | | GPI Ligands | | | | | |
| Htk-L | Elk-L | ELF-1 | Ehk1-L | LERK4 | AL-1 | B61 | |
| 40 | 41 | 24 | 20 | 23 | 21 | 18 | Elk-L3 |
|  | 47 | 20 | 21 | 21 | 18 | 18 | Htk-L |
|  |  | 23 | 20 | 20 | 20 | 22 | Elk-L |
|  |  |  | 42 | 37 | 55 | 41 | ELF-1 |
|  |  |  |  | 38 | 36 | 38 | Ehk1-L |
|  |  |  |  |  | 38 | 34 | LERK4 |
|  |  |  |  |  |  | 41 | AL-1 |

METHOD FOR IDENTIFYING COMPOUNDS THAT INHIBIT OR ENHANCE ACTIVATION OF A TRANSMEMBRANE LIGAND FOR A RECEPTOR TYROSINE KINASE

This application claims priority under 35 U.S.C. §371 to International Application No. PCT/CA97/00473, filed Jul. 4, 1997, which claims priority to U.S. Provisional Application Serial No. 60/021,272, filed Jul. 5, 1996.

FIELD OF THE INVENTION

The invention relates to a method of affecting or modulating a pathway in a cell which is regulated by the binding of a transmembrane ligand for an Elk-related receptor tyrosine kinase and an oligomerized Elk-related receptor tyrosine kinase; a method of identifying substances which affect the binding of a transmembrane ligand for an Elk-related receptor tyrosine kinase and an oligomerized Elk-related receptor tyrosine kinase; and to methods and pharmaceutical compositions using oligomerized Elk-related receptor tyrosine kinases, and substances identified using a method of the invention.

BACKGROUND OF THE INVENTION

Receptor tyrosine kinases play essential roles in cellular signalling events. The largest known family of receptor tyrosine kinases is the Eph subfamily of receptor tyrosine kinases. Eph subfamily tyrosine kinases have been implicated in the control of axon guidance and fasciculation[1-7], in regulating cell migration[8], and in defining compartments in the developing embryo[9-11]. Efficient activation of Eph receptors generally requires that their ligands be anchored to the cell surface, either through a transmembrane (TM) region or a glycosyl phosphatidylinositol (GPI) group[12]. These observations have suggested that Eph receptors can transduce signals initiated by direct cell-cell interactions. Genetic analysis of Nuk, a mouse Eph receptor that binds TM-ligands, has suggested that these ligands have a signalling function[6].

SUMMARY OF THE INVENTION

Challenging cells expressing the transmembrane (TM)-ligands, Elk-L or Htk-L, with the clustered extracellular domain of Nuk was found to induce phosphorylation of the ligands on tyrosine, a process which is mimicked both in vitro and in vivo by an activated Src tyrosine kinase. Co-culturing of cells expressing a TM-ligand with cells expressing Nuk also was shown to lead to tyrosine phosphorylation of both the ligand and Nuk. Therefore TM-ligands are associated with a tyrosine kinase, and are inducibly phosphorylated upon binding the Nuk receptor, in a fashion reminiscent of cytokine receptors. Furthermore, it was shown that TM-ligands, as well as Nuk, are phosphorylated on tyrosine in mouse embryos, indicating that this is a physiological process. These experimental results confirm that Eph receptors and their TM-ligands mediate bi-directional cell signalling.

Therefore, the present invention provides a method of modulating the biological activity of a transmembrane ligand for an Elk-related receptor tyrosine kinase in a cell expressing the transmembrane ligand comprising forming a complex between a purified and isolated oligomerized Elk-related receptor tyrosine kinase, or an isoform or an extracellular domain of the Elk-related receptor tyrosine kinase, and the transmembrane ligand expressed on the cell, thereby modulating the biological activity of the transmembrane ligand.

The present invention also provides a method of affecting or modulating a pathway regulated by a transmembrane ligand for an Elk-related receptor tyrosine kinase in a cell expressing the transmembrane ligand, comprising forming a complex between a purified and isolated oligomerized Elk-related receptor tyrosine kinase, or an isoform or an extracellular domain of the Elk-related receptor tyrosine kinase, and a transmembrane ligand expressed on the cell, thereby affecting or modulating a pathway in the cell which is regulated by the transmembrane ligand.

The invention also provides a method for evaluating a substance for its ability to modulate the biological activity of a transmembrane ligand for an Elk-related receptor tyrosine kinase in a cell expressing the transmembrane ligand comprising the steps of:

(a) contacting an oligomerized Elk-related receptor tyrosine kinase, or an isoform or an extracellular domain of the Elk-related receptor tyrosine kinase; a transmembrane ligand which binds to the Elk-related receptor tyrosine kinase to form a receptor-ligand complex, wherein the transmembrane ligand is a transmembrane ligand for an Elk-related receptor tyrosine kinase expressed on a cell; and, a test substance, under conditions which permit the formation of receptor-ligand complexes;

(b) assaying for receptor-ligand complexes, free Elk-related receptor tyrosine kinase, or non-complexed transmembrane ligand, or for activation of the transmembrane ligand; and (c) comparing to a control to determine if the substance inhibits or enhances the binding of the Elk-related receptor tyrosine kinase and transmembrane ligand, and thereby modulates the biological activity of the transmembrane ligand.

The invention also provides a method for identifying a substance which affects or modulates a pathway regulated by a transmembrane ligand for an Elk-related receptor tyrosine kinase in a cell expressing the transmembrane ligand, comprising the steps of:

(a) contacting an oligomerized Elk-related receptor tyrosine kinase, or an isoform or an extracellular domain of the Elk-related receptor tyrosine kinase; a transmembrane ligand which binds to the Elk-related receptor tyrosine kinase to form receptor-ligand complexes which activate a pathway regulated by a transmembrane ligand for an Elk-related receptor tyrosine kinase in a cell expressing the transmembrane ligand; and a test substance under conditions which permit the formation of receptor-ligand complexes;

(b) assaying for receptor-ligand complexes, free Elk-related receptor tyrosine kinase, or non-complexed transmembrane ligand, or for activation of the transmembrane ligand; and (c) comparing to a control to determine if the substance inhibits or enhances the binding of the Elk-related receptor tyrosine kinase and transmembrane ligand, and thereby affects or modulates the pathway.

The ability of a substance to inhibit or enhance the binding of an oligomerized Elk-related receptor tyrosine kinase and transmembrane ligand correlates with the ability of the substance to inhibit or enhance the biological activity of the transmembrane ligand, including the signal transduction activities of the ligand, and in particular the activation of a pathway regulated by the ligand.

The invention also contemplates a method for evaluating a substance for its ability to inhibit or enhance the interaction of an oligomerized Elk-related receptor tyrosine kinase, or an isoform, or an extracellular domain of the Elk-related receptor tyrosine kinase, and a transmembrane ligand for an Elk-related receptor tyrosine kinase expressed on a cell comprising the steps of:

(a) providing a reporter gene operably linked to a DNA binding site for a transcriptional activator;

(b) providing a first hybrid protein comprising the transmembrane ligand in polypeptide linkage to a DNA binding domain of the transcriptional activator;

(c) providing a second hybrid protein comprising an oligomerized Elk-related receptor tyrosine kinase or an isoform or an extracellular domain of the Elk-related receptor tyrosine kinase in polypeptide linkage to an activation domain of the transcriptional activator; under conditions where the transmembrane ligand and oligomerized Elk-related receptor tyrosine kinase can bind and thereby reconstitute the transcriptional activator which induces transcription of the reporter gene;

(d) administering a test substance; and (e) monitoring expression of the reporter gene, wherein a decrease in expression is an indication that the substance inhibits the interaction of the transmembrane ligand and oligomerized Elk-related receptor tyrosine kinase, and an increase in expression is an indication that the substance enhances the interaction of the transmembrane ligand and oligomerized Elk-related receptor tyrosine kinase. In an alternate method, the oligomerized Elk-related receptor tyrosine kinase is linked to the DNA binding domain, and the transmembrane ligand is linked to the activation domain.

In another aspect, the invention features an antibody preparation which specifically binds to a receptor-ligand complex comprising an oligomerized Elk-related receptor tyrosine kinase, or an isoform or an extracellular domain of the kinase, and a transmembrane ligand for an Elk-related receptor tyrosine kinase.

In another aspect, the invention features a method of purifying a compound which inhibits or enhances the binding of an oligomerized Elk-related receptor tyrosine kinase, or an isoform or an extracellular domain of the kinase, and a transmembrane ligand for an Elk-related receptor tyrosine kinase comprising contacting the compound with one of the ligand or receptor; and, isolating the compound by its binding affinity for the ligand or receptor.

The substances, and compounds obtained using the methods of the invention and the antibodies specific for receptor-ligand complexes may be used to modulate the biological activity of a transmembrane ligand for an Elk-related receptor tyrosine kinase in a cell expressing the transmembrane ligand, including inhibiting or enhancing signal transduction activities of the transmembrane ligand, and in particular modulating a pathway regulated by the transmembrane ligand.

The invention still further provides a method for affecting or modulating neuronal development or regeneration in a subject comprising administering to a subject an effective amount of a purified and isolated oligomerized Elk-related receptor tyrosine kinase, or an isoform or an extracellular domain thereof, a substance or compound identified using a method of the invention, or an antibody specific for a receptor-ligand complex of the invention.

In yet another aspect, the invention provides a method for affecting or modulating axonogenesis in a subject comprising administering to a subject an effective amount of a purified and isolated oligomerized Elk-related receptor tyrosine kinase, or an isoform or an extracellular domain thereof, a substance or compound identified using a method of the invention, or an antibody specific for a receptor-ligand complex of the invention.

The invention also relates to a pharmaceutical composition which comprises a purified and isolated oligomerized Elk-related receptor tyrosine kinase, or an isoform or an extracellular domain thereof, a substance or compound identified using a method of the invention, or an antibody specific for a receptor-ligand complex of the invention, in an amount effective to stimulate or inhibit neuronal development or regeneration and a pharmaceutically acceptable carrier, diluent or excipient.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 1A is an alignment of human Elk-L, Htk-L and Elk-L3 cytoplasmic domains;

FIG. 5A is a composite sequence of cDNAs encoding full length human Elk-L3 and a segment of rat Elk-L3;

FIG. 5C shows in matrix form the percent similarity between ligands in FIG. 5B.

DETAILED DESCRIPTION OF THE INVENTION

As hereinbefore mentioned, the present invention provides a method of modulating the biological activity of a transmembrane ligand for an Elk-related receptor tyrosine kinase in a cell expressing the transmembrane ligand comprising forming a complex between a purified and isolated oligomerized Elk-related receptor tyrosine kinase, or an isoform or an extracellular domain of the kinase, and a transmembrane ligand expressed on the cell. The biological activity of a transmembrane ligand may be modulated by inhibiting or enhancing the signal transduction activities of the ligand including affecting or modulating a pathway regulated by a transmembrane ligand for an Elk-related receptor tyrosine kinase in a cell expressing the transmembrane ligand.

A pathway which is regulated by a transmembrane ligand for an Elk-related receptor tyrosine kinase in a cell expressing the transmembrane ligand refers to a regulatory pathway in the cell that affects, for example gene expression, cell division, cytoskeletal architecture, cell metabolism, migration, cell-cell interactions, and spatial positioning, and which is activated by the binding of transmembrane ligands with an oligomerized Elk-related receptor tyrosine kinase, or an isoform, or an extracellular domain thereof. Examples of such pathways are the GAP/Ras pathway, the pathway that regulates the breakdown of the polyphosphoinositides through phospholipase C (PLC) and the Src/tyrosine kinase and Ras pathways.

Figure 5B:
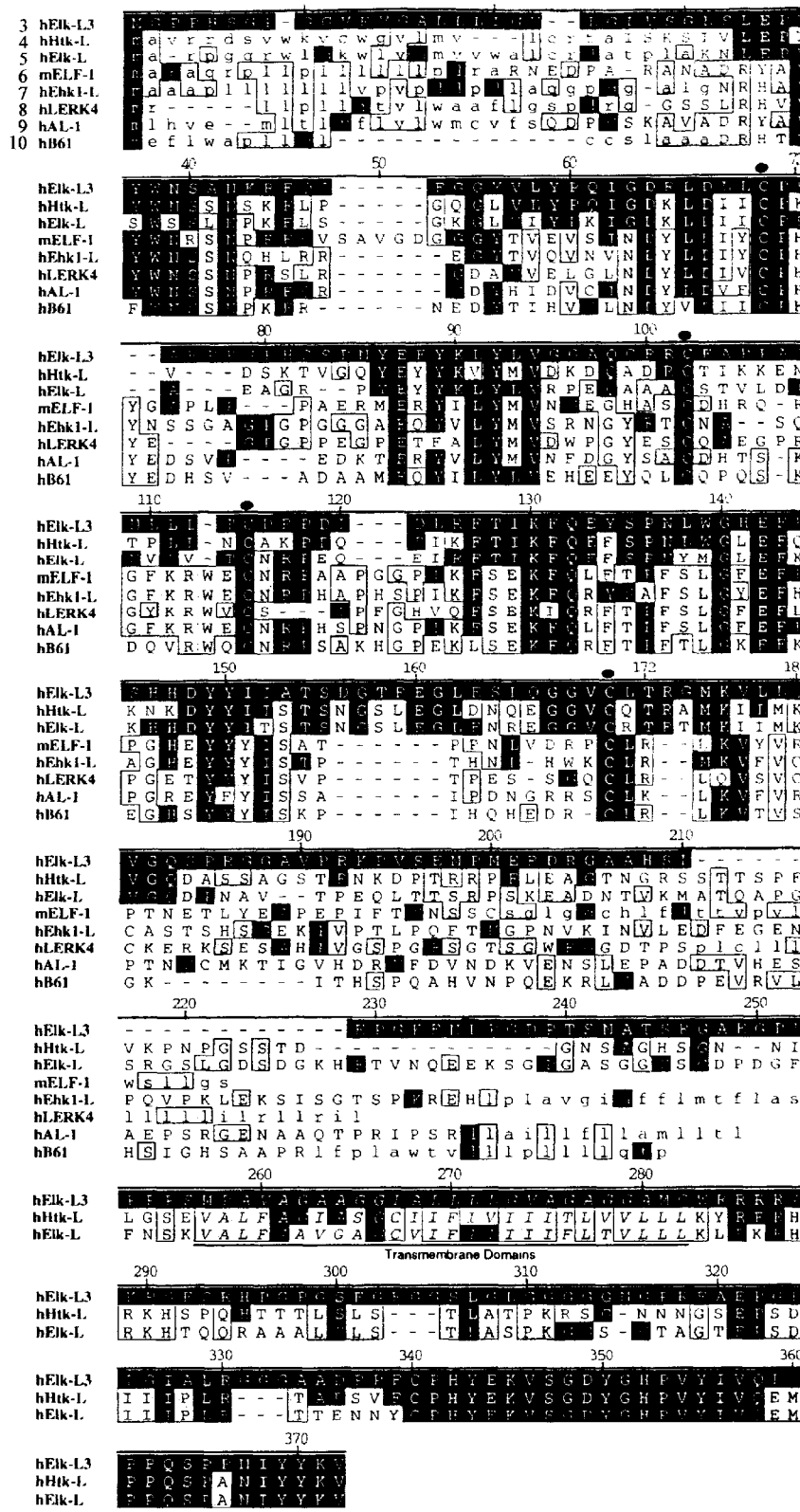
FIG. 5B shows amino acid sequences of all the known Eph family ligands aligned with each other, using the human versions with the exception of mouse ELF-1.

"Transmembrane ligand or transmembrane ligands" refers to a class of ligands which are anchored to the cell membrane through a transmembrane domain, and bind to the extracellular domain of an Eph subfamily receptor tyrosine kinase, facilitating dimerization and autophosphorylation of the receptor. The transmembrane ligands which are targeted or used in accordance with the methods of the invention are those that bind to and preferably activate (i.e. phosphorylate) an Elk-related receptor tyrosine kinase (see discussion of the Elk-related receptor tyrosine kinases below). Preferably the transmembrane ligands used in the methods of the invention are Elk-L/LERK2/Efl-3/Cek5-L; hHtk-L/ELF-2/Lerk5 (Tessier-Lavingne, M., 1995, Cell, 82:345–348) and hElk-L3/Efl6 (Gale et al.). These transmembrane ligands have a highly conserved cytoplasmic region with multiple potential sites for tyrosine phosphorylation[12-17]. The amino acid sequences for the transmembrane ligands hElk-L3, hHtk-L, and hElk-L, and the cytoplasmic, transmembrane, and extracellular domains of the ligands are shown in FIG. 5 (SEQ. ID. NOS. 1–9), which is FIG. 1 in Gale, N. W. et al., 1996.

Transmembrane ligands which may be selected or targeted in accordance with the present invention also include (i) proteins having sequence identity with known transmembrane ligands such as hElk-L3, hHtk-L, and hElk-L, and their homologs; (ii) proteins which can bind with the extracellular domain of an Elk-related receptor tyrosine kinase; and (iii) chimeric proteins of transmembrane ligands, e.g. a protein containing a cytoplasmic domain of one transmembrane ligand and an extracellular domain from a different transmembrane ligand.

The term "Elk-related receptor tyrosine kinase" refers to a particular subclass of the Eph subfamily of receptor tyrosine kinases. The Eph subfamily receptor tyrosine kinases are a closely related group of transmembrane receptor tyrosine kinases which contain cell adhesion-like domains on their extracellular structurally related cysteine rich extracellular domain containing a single immunoglobulin (Ig)-like loop near the N-terminus and two fibronectin III (FN III) repeats adjacent to the plasma membrane. For example, Nuk contains 20 cysteine residues whose position is conserved in the extracellular domain of Eph family members, an immunoglobulin-like domain near the amino terminus (Ig-like), and two fibronectin type III repeats (FN III; between Nuk amino acids residues 330–420 and 444–534). The Ig-like domain of Nuk contains specific residues (Cys$^{70}$, Trp$^{80}$, Cys$^{115}$) known to be conserved in the Ig superfamily (Williams and Barclay, Ann. Rev. Immunol. 6:381–405, 1988).

The Elk-related receptor tyrosine kinases bind to, and are phosphorylated by transmembrane ligands, and include mouse Nuk and its homologs namely, Hek5 and Erk in humans, Sek3 in mice, and Cek5 in chickens; rat Elk and its homologs including Cek6a in chickens and xEK; human Hek2 and its homologs including Sek4 in mice and Cek10 in chickens; and human Htk and its homologs including Myk1 in mice. The amino acid sequences for representative Elk-related receptor tyrosine kinases can be found in GenBank, for example Accession Nos. L25890 (Nuk), X13411 (rat Elk), U07695 (human Htk), M83941 (Hek), and the publications referred to therein.

Homologs of Elk-related receptor tyrosine kinases are identified by aligning a sequence of a putative homolog with a known Elk-related receptor tyrosine kinase and comparing the positions in each sequence. When a position in the compared sequence is occupied by the same nucleotide base or amino acid, then the molecules are matching or have identical positions shared by the sequences. Kinase proteins which may be used in the methods and compositions of the invention may have over 60%, preferably over 70%, most preferably over 80% identity with an Elk-related receptor tyrosine kinase.

Isoforms of an Elk-related receptor tyrosine kinase may be used in the methods and compositions of the invention. Generally, an isoform contains the same number and kinds of amino acids and it binds to a transmembrane ligand as described herein, but the isoform has a different molecular structure.

An extracellular domain of an Elk-related receptor tyrosine kinase may also be used in the methods and compositions of the invention. The extracellular domain of an Elk-related receptor tyrosine kinase is generally defined as the region extracellular to the transmembrane domain. Specifically it is characterised by a cysteine rich region, whose position is conserved in the extracellular domain of Eph receptor family members, an immunoglobulin-like domain near the amino terminus (Ig-like), and two fibronectin type III repeats (FN III). An extracellular domain of an Elk-related receptor tyrosine kinases may be selected based on these characteristic features and by comparing the amino acid sequences of the extracellular domains of known Elk-related receptor tyrosine kinases.

An Elk-related receptor tyrosine kinase may be selected for use in a method or composition of the invention based on the nature of the transmembrane ligand which is targeted or selected. The selection of a specific complementary ligand and Elk-related receptor tyrosine kinase (e.g. Elk-L and Elk or Nuk; and Htk-L and Elk or Nuk) in a method of the invention may allow for the identification of a specific substance that affects a pathway regulated by a specific transmembrane ligand.

An Elk-related receptor tyrosine kinase or extracellular domain thereof, or a transmembrane ligand may be isolated from cells which are known to express the proteins. Alternatively the protein or part of the protein may be prepared using conventional recombinant DNA methods (e.g. baculovirus expression in insect cells). The proteins or parts thereof may also be prepared by chemical synthesis using standard techniques such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

The Elk-related receptor tyrosine kinase protein or extracellular domain thereof, or transmembrane ligands may also be expressed on the surface of a cell (e.g. Cos-1 cell) using conventional methods.

An Elk-related receptor tyrosine kinase or extracellular domain thereof, or transmembrane ligand may be conjugated with other molecules, such as proteins or polypeptides. For example, N-terminal fusion proteins may be synthesized by fusing, through recombinant techniques, the N-terminal of an Elk-related receptor tyrosine kinase or extracellular domain thereof, and the sequence of a selected protein or marker protein with a desired biological function, such as an oligomerization motif which facilitates oligomerization of the receptor or ligand. Examples of oligomerization motifs include immunoglobulins, and parts thereof such as the constant region of an immunoglobulin; and motifs which introduce reactive groups which provide for hydrophobic interactions between receptors or ligands, for example, amphoteric α-helices.

The transmembrane ligands and Elk-related receptor tyrosine kinase or extracellular domain thereof, or fusions thereof, used in the methods and compositions of the invention are oligomerized. An Elk-related receptor tyrosine kinase or extracellular domain thereof, or transmembrane ligands may be dimerized by preparing fusion proteins as discussed above containing an oligomerization motif such as a constant region of an immunoglobulin. Clusters of receptors or ligands may then optionally be prepared by adding antibodies specific for the constant region of the immunoglobulin. For example, a Nuk extracellular domain-IgG constant chain fusion protein may be clustered using anti-human IgG. If the receptor tyrosine kinase or transmembrane ligand is associated with a cell, interaction of the receptor or extracellular domain thereof with a transmembrane ligand will result in dimerization of the receptor or ligand.

The invention provides a method for evaluating a substance for its ability to modulate the biological activity of a transmembrane ligand for an Elk-related receptor tyrosine kinase in a cell expressing the transmembrane ligand. The method involves contacting an oligomerized Elk-related receptor tyrosine kinase, or an isoform or an extracellular domain of the Elk-related receptor tyrosine kinase; a transmembrane ligand for an Elk-related receptor tyrosine kinase expressed on a cell that binds to the Elk-related receptor tyrosine kinase to form a receptor-ligand complex; and, a test substance, under conditions which permit the formation of receptor-ligand complexes. Receptor-ligand complexes, free Elk-related receptor tyrosine kinase, or non-complexed transmembrane ligand, or activation of the transmembrane ligand are assayed. The results are compared to a control to determine if the substance inhibits or enhances the binding of the Elk-related receptor tyrosine kinase and transmembrane ligand, and thereby modulates the biological activity of the transmembrane ligand.

In an embodiment, the invention provides a method for identifying a substance which affects or modulates a pathway regulated by a transmembrane ligand for an Elk-related receptor tyrosine kinase in a cell expressing the transmembrane ligand. An oligomerized Elk-related receptor tyrosine kinase, or an isoform or an extracellular domain of the Elk-related receptor tyrosine kinase, is contacted with a test substance, and a transmembrane ligand which binds to the receptor to form receptor-ligand complexes which activate the pathway, under conditions which permit the formation of receptor-ligand complexes. Receptor-ligand complexes, free Elk-related receptor tyrosine kinase, or non-complexed transmembrane ligands, or activation of the ligand are assayed and the results are compared to a control to determine the effect of the substance.

A substance identified using a method of the invention may stimulate or inhibit the binding of an oligomerized Elk-related receptor tyrosine kinase, or an isoform or an extracellular domain thereof, and transmembrane ligands, or compete for a site on the oligomerized Elk-related receptor tyrosine kinase which binds the transmembrane ligands or a site on the transmembrane ligands which binds to the oligomerized Elk-related receptor tyrosine kinase. The substance may be an endogenous physiological substance, or it may be a natural or synthetic drug.

Oligomerized Elk-related receptor tyrosine kinases that may be used in the methods of the invention are described herein. In particular, an oligomerized extracellular domain of an Elk-related receptor tyrosine kinase, preferably Nuk, can be employed in the method. The oligomerized extracellular domain may also be prepared as a fusion protein as described herein. The Elk-related receptor tyrosine kinase may be associated with a cell which either exogenously expresses the kinase (e.g. transformed Cos-b 1cells which express the kinase) or a cell which endogenously expresses the kinase (e.g. Cos-1 monkey kidney cells endogenously expressing Nuk).

The transmembrane ligand used in the methods of the invention may be a ligand which is native to the selected oligomerized Elk-related receptor tyrosine kinase, or it may be a ligand which is not native to the selected receptor tyrosine kinase. The transmembrane ligand is preferably associated with a cell which either exogenously expresses the ligand (e.g. transformed Cos-1 cells) or a cell which endogenously expresses the ligand (e.g. CHP-100 cells which express the transmembrane ligand Elk-L). Where the transmembrane ligand used in a method of the invention is not cell associated, it should be oligomerized using the methods described herein.

Conditions which permit the formation of receptor-ligand complexes may be selected having regard to factors such as the nature and amounts of the receptor and the ligand.

The receptor-ligand complex, free oligomerized receptor or non-complexed transmembrane ligand may be isolated by conventional isolation techniques, for example, salting out, chromatography, electrophoresis, gel filtration, fractionation, absorption, polyacrylamide gel electrophoresis, agglutination or combinations thereof.

Antibody against the ligand or the receptor, or a labelled ligand, or a labelled oligomerized receptor may be utilized in the methods of the invention to facilitate isolation of the complexes etc. The antibodies the oligomerized receptor, or substance may be labelled with a detectable substance.

The receptor or ligand used in the method of the invention may be insolubilized. For example, the receptor or ligand may be bound to a suitable carrier including agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized receptor or ligand may be prepared by reacting the material with a suitable insoluble carrier using known chemical or physical methods, for example, cyanogen bromide coupling.

Where the ligand is expressed on the surface of a cell the affect of a test substance may be determined by assaying for activation of the ligand, or by assaying for a biological affect on the cell. Activation of the ligand may be determined by assaying for phosphorylation of the ligand.

The interaction of the receptor and ligand may be identified using a two-hybrid expression system wherein the activity of a transcriptional activator is reconstituted. (See for example, Chien et al. 1991, Proc. Natl. Acad. Sci. (USA) 88:9578 re two-hybrid systems). The system may comprise a reporter gene (e.g. genes encoding gene products such as β-galactosidase (e.g. lacZ), luciferase, alkaline phosphatase, horseradish peroxidase), operably linked to a DNA binding site for a transcriptional activator; a first hybrid protein comprising a transmembrane ligand for an Elk-related receptor tyrosine kinase in polypeptide linkage to a DNA binding domain of a transcriptional activator; and a second hybrid protein comprising an oligomerized Elk-related receptor tyrosine kinase or an isoform or an extracellular domain of the Elk-related receptor tyrosine kinase, in polypeptide linkage to an activation domain of the transcriptional activator. The system is carried out employing conditions that allow binding of the transmembrane ligand and oligomerized Elk-related receptor tyrosine kinase thereby reconstituting the transcriptional activator which induces transcription of the reporter gene. A test substance is added, and the expression of the reporter gene is monitored. A decrease in expression is an indication that the substance inhibits the interaction of the transmembrane ligand and oligomerized Elk-related receptor tyrosine kinase, and an increase in expression is an indication that the substance enhances the interaction of the transmembrane ligand and oligomerized Elk-related receptor tyrosine kinase. In an alternate method, the oligomerized Elk-related receptor tyrosine kinase is linked to the DNA binding domain, and the transmembrane ligand is linked to the activation domain.

The invention also provides host organisms (typically unicellular organisms) which harbor a two-hybrid system as described herein. Usually the host organism is a yeast cell such as *Saccharomyces cervisiae*.

In a particular system, the yeast GAL4 protein which has a domain responsible for DNA-binding and another domain for transcriptional activation is employed. In the expression system, plasmids encoding two hybrid proteins one containing the GAL4 DNA binding domain fused to a first protein (a transmembrane ligand or an oligomerized Elk-related receptor tyrosine kinase), and a second plasmid containing the GAL4 activation domain fused to a second protein (a transmembrane ligand or an oligomerized Elk-related receptor tyrosine kinase which forms a complex with the first protein) are introduced into the yeast. If the first and second proteins interact with one another, the ability to activate transcription from promoters containing GAL4-binding sites is reconstituted leading to the expression of a reporter gene e.g. lacZ.

The invention also features an antibody preparation which specifically binds to a receptor-ligand complex comprising an oligomerized Elk-related receptor tyrosine kinase, or an isoform or an extracellular domain of the kinase, and a transmembrane ligand for an Elk-related receptor tyrosine kinase. Antibodies (e.g. monoclonal and polyclonal antibodies) may be prepared against oligomerized receptor-ligand complexes. The invention can employ not only intact monoclonal or polyclonal antibodies, but also immunologically active fragments (e.g. a Fab or (Fab)$_2$ fragment), an antibody heavy chain, and antibody light chain, a genetically engineered single chain $F_v$ molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art.

The invention also features a method of purifying a compound which inhibits or enhances the binding of an oligomerized Elk-related receptor tyrosine kinase, or an isoform or an extracellular domain of the kinase, and a transmembrane ligand for an Elk-related receptor tyrosine kinase comprising contacting the compound with one of the ligand or receptor; and, isolating the compound by its binding affinity for the ligand or receptor. Conventional affinity binding methods can be used to isolate a compound.

The substances and compounds obtained using the methods of the invention, and the antibodies specific for receptor-ligand complexes may be used to modulate the biological activity of a transmembrane ligand for an Elk-related receptor tyrosine kinase in a cell expressing the transmembrane ligand, including inhibiting or enhancing signal transduction activities of the transmembrane ligand, and in particular modulating a pathway in a cell regulated by a transmembrane ligand for an Elk-related receptor tyrosine kinase, particularly those pathways involved in neuronal development, axonal migration, pathfinding and regeneration. The identification and isolation of substances and compounds will permit studies of the role of the substances and compounds in the developmental regulation of axonogenesis and neural regeneration, and permit the development of substances which affect these roles, such as functional or non-functional analogues of the oligomerized extracellular domain of an Elk-related receptor tyrosine kinase. The substances, compounds, and substances derived therefrom, and antibodies, will be useful as pharmaceuticals to modulate axonogenesis, nerve cell interactions and regeneration, to treat conditions such as neurodegenerative diseases and conditions involving trauma and injury to the nervous system, for example Alzheimer's disease, Parkinson's disease, Huntington's disease, demylinating diseases, such as multiple sclerosis, amyotrophic lateral sclerosis, bacterial and viral infections of the nervous system, deficiency diseases, such as Wernicke's disease and nutritional polyneuropathy, progressive supranuclear palsy, Shy Drager's syndrome, multistem degeneration and olivo ponto cerebellar atrophy, peripheral nerve damage, trauma and ischemia resulting from stroke.

The present invention thus provides a method for affecting neuronal development or regeneration in a subject comprising administering to a subject an effective amount of a purified and isolated oligomerized Elk-related receptor tyrosine kinase, or an isoform or an extracellular domain thereof, a substance or compound identified using a method of the invention, or antibodies specific for oligomerized receptor-ligand complexes. The invention also contemplates a method for stimulating or inhibiting axonogenesis in a subject comprising administering to a subject an effective amount of a purified and isolated oligomerized Elk-related receptor tyrosine kinase protein, or an isoform or an extracellular domain thereof, a substance or compound identified using a method of the invention, or antibodies specific for oligomerized receptor-ligand complexes.

The invention still further relates to a pharmaceutical composition which comprises a purified and isolated oligomerized Elk-related receptor tyrosine kinase protein or an isoform or an extracellular domain thereof, a substance or compound identified using a method of the invention, or antibodies specific for oligomerized receptor-ligand complexes, in an amount effective to regulate neuronal development or regeneration and a pharmaceutically acceptable carrier, diluent or excipient. The pharmaceutical compositions may be used to stimulate or inhibit neuronal development regeneration and axonal migration associated with neurodegenerative conditions and conditions involving trauma and injury to the nervous system as described above.

The compositions of the invention are administered to subjects in a biologically compatible form suitable for pharmaceutical administration in vivo. By "biologically compatible form suitable for administration in vivo" is meant a form of the protein to be administered in which any toxic effects are outweighed by the therapeutic effects of the protein. The term subject is intended to include mammals and includes humans, dogs, cats, mice, rats, and transgenic species thereof. Administration of a therapeutically active amount of the pharmaceutical compositions of the present invention is defined as an amount effective, at dosages and for periods of time necessary to achieve the desired result. For example, a therapeutically active amount of an oligomerized Elk-related receptor tyrosine kinase protein may vary according to factors such as the condition, age, sex, and weight of the individual. Dosage regimes may be adjusted to provide the optimum therapeutic response. For example, several divided doses may be administered daily or the dose may be proportionally reduced as indicated by the exigencies of the therapeutic situation.

The active compound (e.g., protein) may be administered in a convenient manner such as by injection (subcutaneous, intravenous, etc.), oral administration, inhalation, transdermal application, or intracerebral administration. Preferably, the pharmaceutical compositions of the invention are administered directly to the peripheral or central nervous system, for example by administration intracerebrally.

A pharmaceutical composition of the invention can be administered to a subject in an appropriate carrier or diluent, co-administered with enzyme inhibitors or in an appropriate carrier such as microporous or solid beads or liposomes. The term "pharmaceutically acceptable carrier" as used herein is intended to include diluents such as saline and aqueous buffer solutions. Liposomes include water-in-oil-in-water emulsions as well as conventional liposomes (Strejan et al., (1984) J. Neuroimmunol 7:27). The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms. Depending on the route of administration, the active compound may be coated to protect the compound from the action of enzymes, acids and other natural conditions which may inactivate the compound.

The pharmaceutical compositions may be administered locally to stimulate axonogenesis and pathfinding, for example the compositions may be administered in areas of local nerve injury or in areas where normal nerve pathway development has not occurred. The pharmaceutical compositions may also be placed in a specific orientation or alignment along a presumptive pathway to stimulate axon pathfinding along that line, for example the pharmaceutical compositions may be incorporated on microcarriers laid down along the pathway. In particular, the pharmaceutical compositions of the invention may be used to stimulate formation of connections between areas of the brain, such as between the two hemispheres or between the thalamus and ventral midbrain. The pharmaceutical compositions may be used to stimulate formation of the medial tract of the anterior commissure or the habenular interpeduncle.

Therapeutic administration of polypeptides may also be accomplished using gene therapy, A nucleic acid including a promoter operatively linked to a heterologous polypeptide may be used to produce high-level expression of the polypeptide in cells transfected with the nucleic acid. DNA or isolated nucleic acids may be introduced into cells of a subject by conventional nucleic acid delivery systems. Suitable delivery systems include liposomes, naked DNA, and receptor-mediated delivery systems, and viral vectors such as retroviruses, herpes viruses, and adenoviruses.

The following non-limiting example is illustrative of the present invention:

EXAMPLE

The following is a detailed description of FIGS. 1 to 4 including a detailed description of the methods utilized in the experiments illustrated in the Figures and outlined in the Example:

Phosphorylation of transmembrane ligands by v-Src. (FIG. 1A) Alignment of human Elk-L, Htk-L and Elk-L3 cytoplasmic domains. Black boxes indicate residues conserved in all TM-ligands; grey boxes indicate residues conserved in two ligands. Conserved tyrosines are marked by an asterisk. Mouse Htk-L cytoplasmic domain is identical to human Htk-L except for a serine to glycine substitution at position 278. Elk-L is also referred to as Lerk-2[13] and Cek5-L[14], Htk-L as Lerk-5[23] and Elf-2[15]. (FIG. 1B) Phosphorylation of GST-hElk-L cytoplasmic domain fusion protein (GST-Elk-L cyt) in vitro by v-Src. v-Src was immunoprecipitated from v-Src transformed Rat-2 cells and incubated with GST fusion proteins or enolase as exogenous substrates in the presence of $^{32}P\gamma ATP$. (FIG. 1C) and (FIG. 1D) Tyrosine phosphorylation of TM-ligands upon coexpression with v-Src. (FIG. 1C) Elk-L and Htk-L were expressed either alone or with v-Src in Cos-1 cells and immunoprecipitated with anti-ligand antibody. Upper panel: anti-phosphotyrosine blot; lower panel: anti-ligand blot (reprobe). (FIG. 1D) TM-ligands were expressed as in (FIG. 1C), precipitated using a Nuk extracellular domain IgG fusion protein (Nuk-Fc) as an affinity reagent, and immunoblotted with anti-phosphotyrosine serum. The band observed at ~100 kDa represents cross-reaction of Nuk-Fc with the protein A-HRP. Methods: (FIG. 1B) v-Src was immunoprecipitated from v-Src transformed Rat-2 cells using an anti-Src monoclonal antibody (Oncogene Science) and immune complexes were incubated for 15 minutes at RT with 5 $\mu$Ci of $^{32}P\gamma ATP$ in Src-KRB[26] alone or in buffer containing enolase, 10 $\mu$g purified GST or GST-Elk-L cyt (residues 262–343 of hElk-L[12]) as exogenous substrates. Proteins were separated on a 10% SDS-PAGE gel and $^{32}P$ labelled proteins were detected by autoradiography. (FIG. 1C) and (FIG. 1D) Cos-1 cells were transiently transfected as indicated with 5 $\mu$g of hElk-L, mHtk-L or v-Src cDNA expression vectors, either alone or in combination, or with empty control vector. Cells were serum starved for approximately 20 hours in medium containing 0.5% foetal bovine serum (FBS) and lysed in PLC lysis buffer[2] at approximately 60 hours post transfection. TM-ligands were precipitated using (FIG. 1C) anti-ligand serum (raised against residues 326–343 of hElk-L, which also recognises Htk-L; Santa Cruz) or (FIG. 1D) 10 $\mu$g of Nuk-Fc fusion protein[11] plus protein A sepharose. Precipitated proteins were washed three times in HNTG[2], separated on a 10% SDS-PAGE gel, transferred to PVDF membrane (Millipore) and immunoblotted with (FIG. 1C) monoclonal (4G10) or (FIG. 1D) polyclonal anti-phosphotyrosine antibodies. Detection was by Enhanced Chemiluminescence (Pierce). In (FIG. 1C) the filter was stripped using 0.1 M glycine pH 2.5 and reprobed with anti-ligand serum.

Figure 2A:
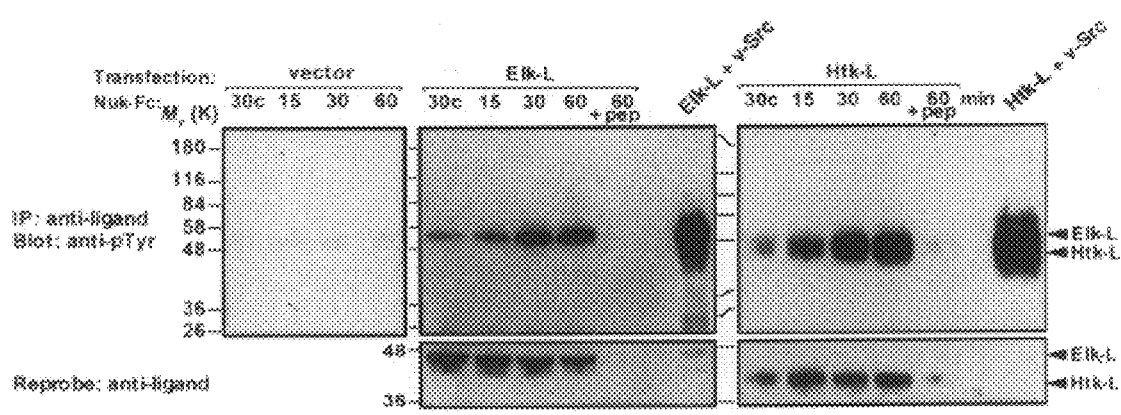
FIG. 2A are immunoblots showing induction of tyrosine phosphorylation of TM-ligands, expressed in Cos-1 cells, upon stimulation with clustered Nuk-Fc.

Stimulation of Tyrosine Phosphorylation of TM-ligands by Nuk Extracellular Domain and Nuk-expressing Cells FIG. 2A: Induction of tyrosine phosphorylation of TM-ligands, expressed in Cos-1 cells, upon stimulation with clustered Nuk-Fc. Cos-1 cells were transiently transfected with Elk-L, Htk-L, or control expression vectors and treated with 2 µg/ml clustered Nuk-Fc fusion protein or Fc tag alone (c) for the indicated periods of time. Cells were lysed, immunoprecipitated with anti-ligand serum and blotted with antibodies to phosphotyrosine (upper panels). Filters were stripped and reprobed with anti-ligand serum (lower panels). As a control, excess immunizing peptide was included as indicated (+pep). Elk-L and Htk-L phosphorylated by cotransfection with v-Src were included on these gels to indicate the mobility of tyrosine phosphorylated ligands; as less protein was loaded in these lanes than the Nuk-Fc stimulated lanes, no bands were detected upon reprobing with anti-ligand serum.

Figure 2B:
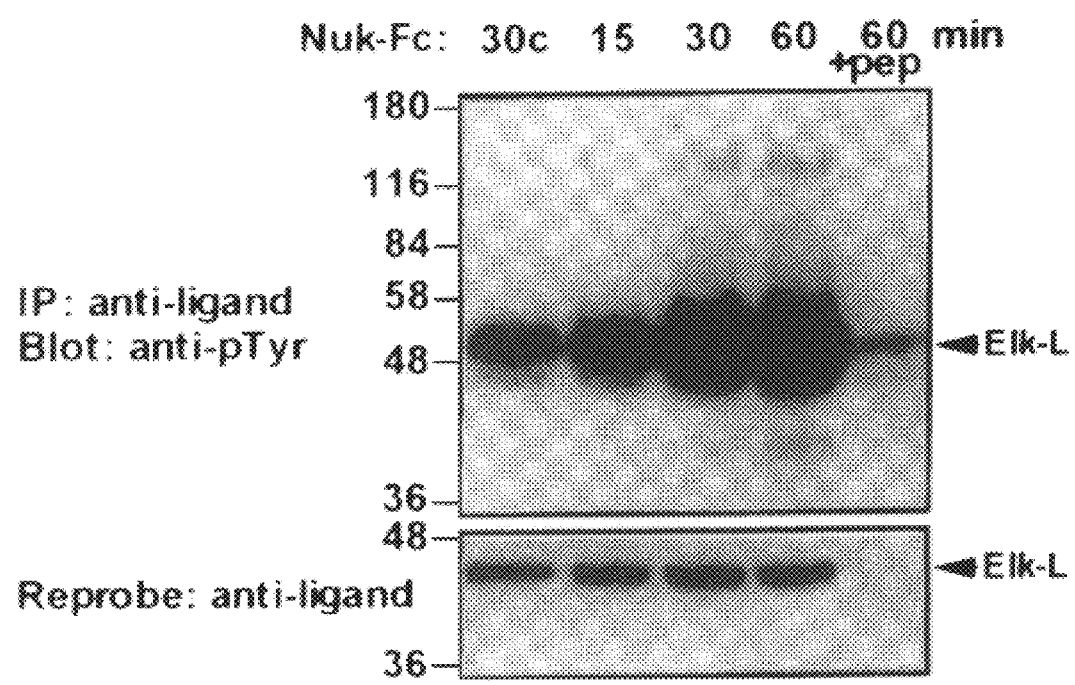
FIG. 2B is an immunoblot showing stimulation of Elk-L tyrosine phosphorylation by Nuk-Fc in CHP-100 cells, which express endogenous Elk-L.

FIG. 2B: Stimulation of Elk-L tyrosine phosphorylation by Nuk-Fc in CHP-100 cells, which express endogenous Elk-L. Cells were stimulated with 2 µg/ml clustered Nuk-Fc or Fc alone (c) for the indicated periods of time, lysed and immunoblotted as in FIG. 2A. Upper panel: anti-phosphotyrosine blot; lower panel: anti-ligand blot (reprobe).+Pep=+competing immunizing peptide.

Figure 1B:
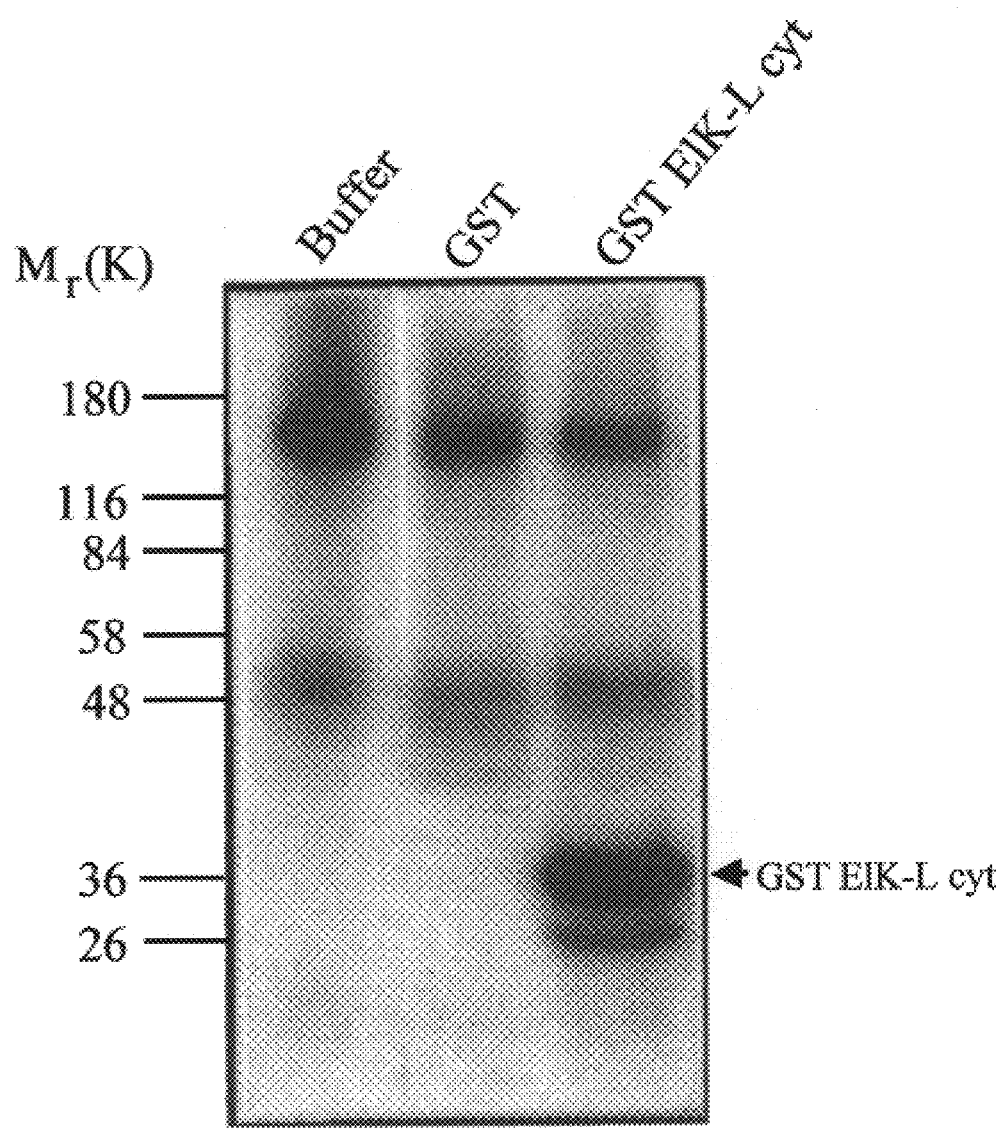
FIG. 1B is an immunoblot showing phosphorylation of GST-hElk-L cytoplasmic domain fusion protein (GST-Elk-L cyt) in vitro by v-Src.
Figure 1C:
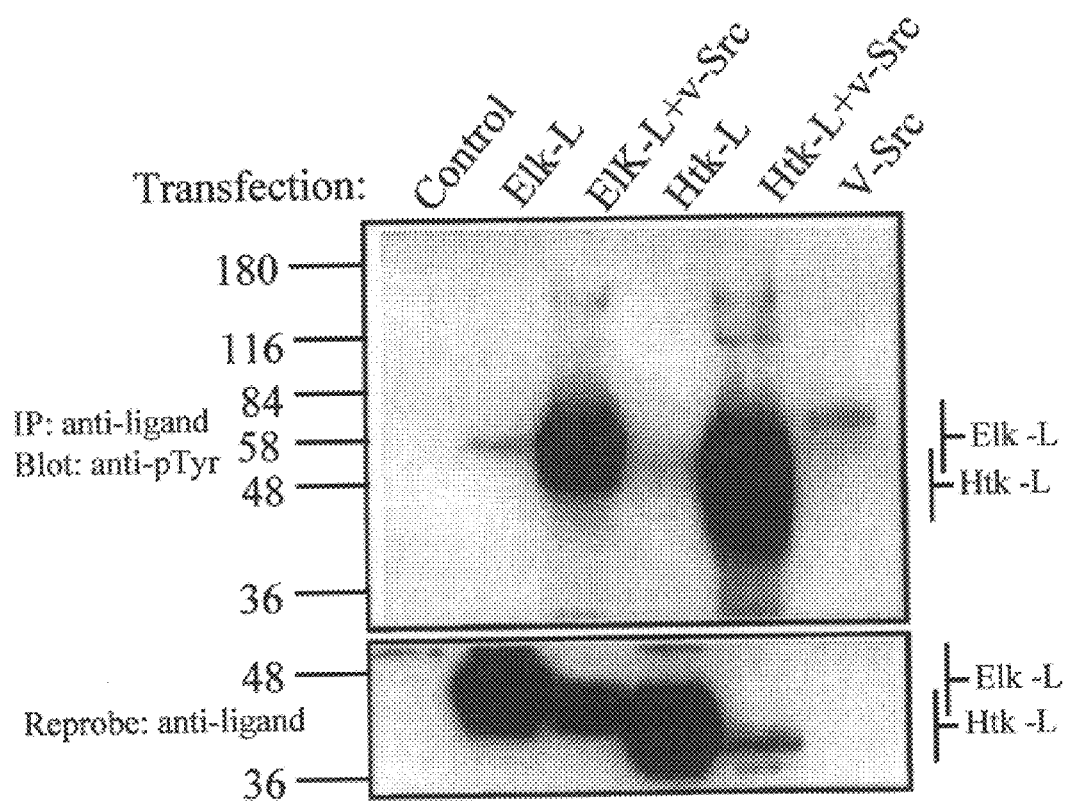
FIG. 1C is an immunoblot showing expression of Elk-L and Htk-L either alone or with v-Src in Cos-1 cells.
Figure 1D:
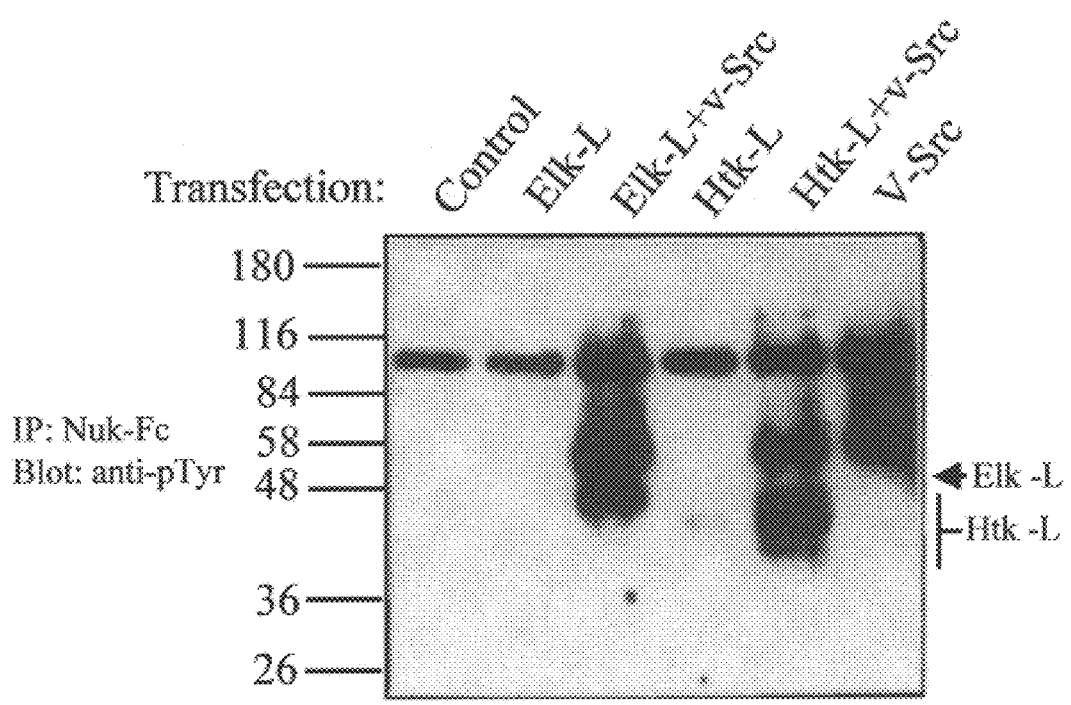
FIG. 1D is an immunoblot showing expression of TM-ligands either alone or with v-Src in Cos-1 cells.
Figure 2C:
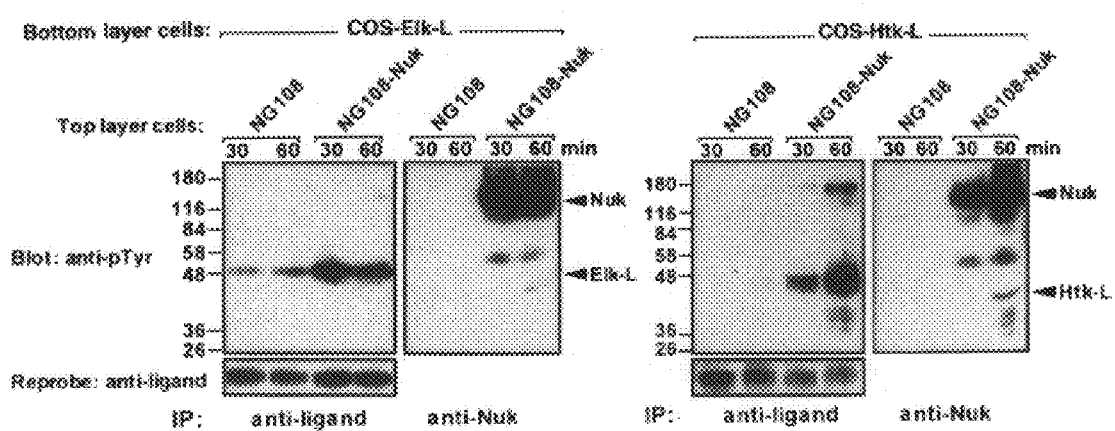
FIG. 2C are immunoblots showing bi-directional signalling between Nuk-expressing NG108 cells and TM-ligand-expressing cells in co-culture.

FIG. 2C: Bi-directional signalling between Nuk-expressing and TM-ligand-expressing cells in co-culture. Cos-1 cells transiently transfected with Elk-L or Htk-L were co-cultured with parental or Nuk-expressing NG108 cells for the indicated times. Left panels: anti-ligand IP; right panels: anti-Nuk IP from pooled, cocultured cells. Upper panels: anti-phosphotyrosine blots; lower panels: anti-ligand blots (reprobe). Methods: In FIG. 2A and FIG. 2B, Cos-1 cells were transiently transfected and serum starved as in FIG. 1. Human neuroepithelial CHP-100 cells were serum starved for 8 hours in medium containing 0.5% FBS. Nuk-Fc[11] or Fc tag (c) was clustered using anti-human IgG (Jackson Immunoresearch) for 1–2 hours at 4° C., diluted to a final concentration of 2 µg/ml in serum free medium, and applied to cells for the indicated periods of time. Cells were lysed in PLC lysis buffer and immunoprecipitated with anti-ligand antibodies. Immunoprecipitation of TM-ligands was inhibited where indicated by addition of 100-fold excess immunizing Elk-L C-terminal peptide (+pep; residues 326–343 of hElk-L, Santa Cruz). Immune complexes were separated and transferred as in FIG. 1 and immunoblotted with monoclonal anti-phosphotyrosine antibodies (4G 10; upper panel). In FIG. 2C, NG 108-15 cells (NG108: mouse neuroblastoma x rat glioma fusion[20]) were stably transfected with an expression vector containing full-length Nuk, and individual G418 resistant clones were isolated (NG108-Nuk). Parental or Nuk-expressing NG108 cells were removed from the plate by tituration and resuspended in PBS+ magnesium and calcium. Cell suspensions were placed on top of serum starved Cos-1 cells transiently expressing Elk-L (left panels) or Htk-L (right panels). Cells were cocultured for 30 or 60 minutes at 37° C., 5% $CO_2$ and lysed together in PLC lysis buffer. Cleared lysates were divided in two and immunoprecipitated with either anti-ligand or anti-Nuk serum[2] as indicated. Proteins were separated and transferred as in FIG. 2 and immunoblotted with monoclonal anti-phosphotyrosine antibodies (upper panels). Blots were stripped and reprobed with anti-ligand antibodies (lower panel).

Figure 3:
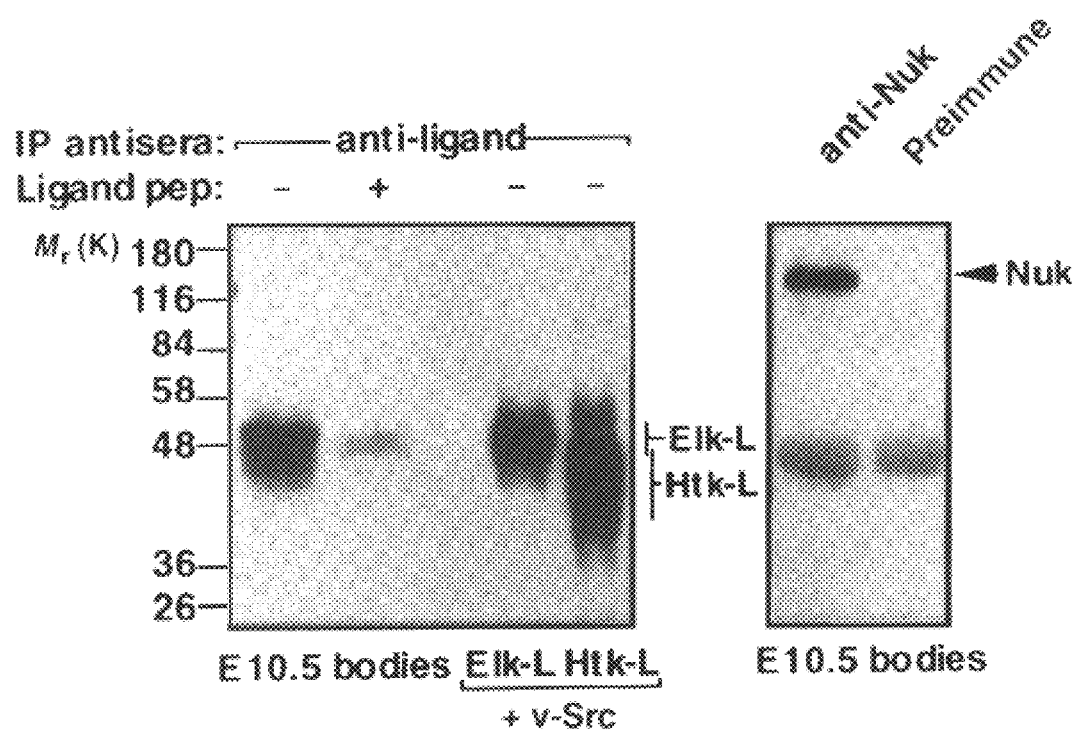
FIG. 3 is an anti-phosphotyrosine immunoblot of TM-ligands and Nuk receptor immunoprecipitated from E10.5 mouse body tissue.

FIG. 3. Both transmembrane ligands and Nuk are phosphorylated on tyrosine in the mouse embryo. Anti-phosphotyrosine immunoblot of TM-ligands (left panel) and Nuk receptor (right panel) immunoprecipitated from E10.5 mouse body tissue. Lysed tissue was immunoprecipitated with anti-Nuk or pre-immune serum (PI), or anti-ligand antibodies with or without addition of excess competing immunizing peptide (ligand pep). The mobility of tyrosine phosphorylated Elk-L and Htk-L is indicated by inclusion of v-Src phosphorylated TM-ligands on the gel (Elk-L+v-Src and Htk-L+v-Src). Methods: E10.5 mouse embryos from wild-type matings were harvested and divided into heads and bodies. Tissue was lysed in PLC lysis buffer by Dounce homogenisation, cleared and precleared by incubation with protein A sepharose. Supernatants were immunoprecipitated with anti-Nuk or pre-immune serum, or anti-ligand antibodies with or without addition of 100-fold excess competing ligand C-terminal peptide. Proteins were separated, transferred and immunoblotted with monoclonal antiphosphotyrosine antibodies. Results for E10.5 head tissue were essentially identical.

Figure 4:
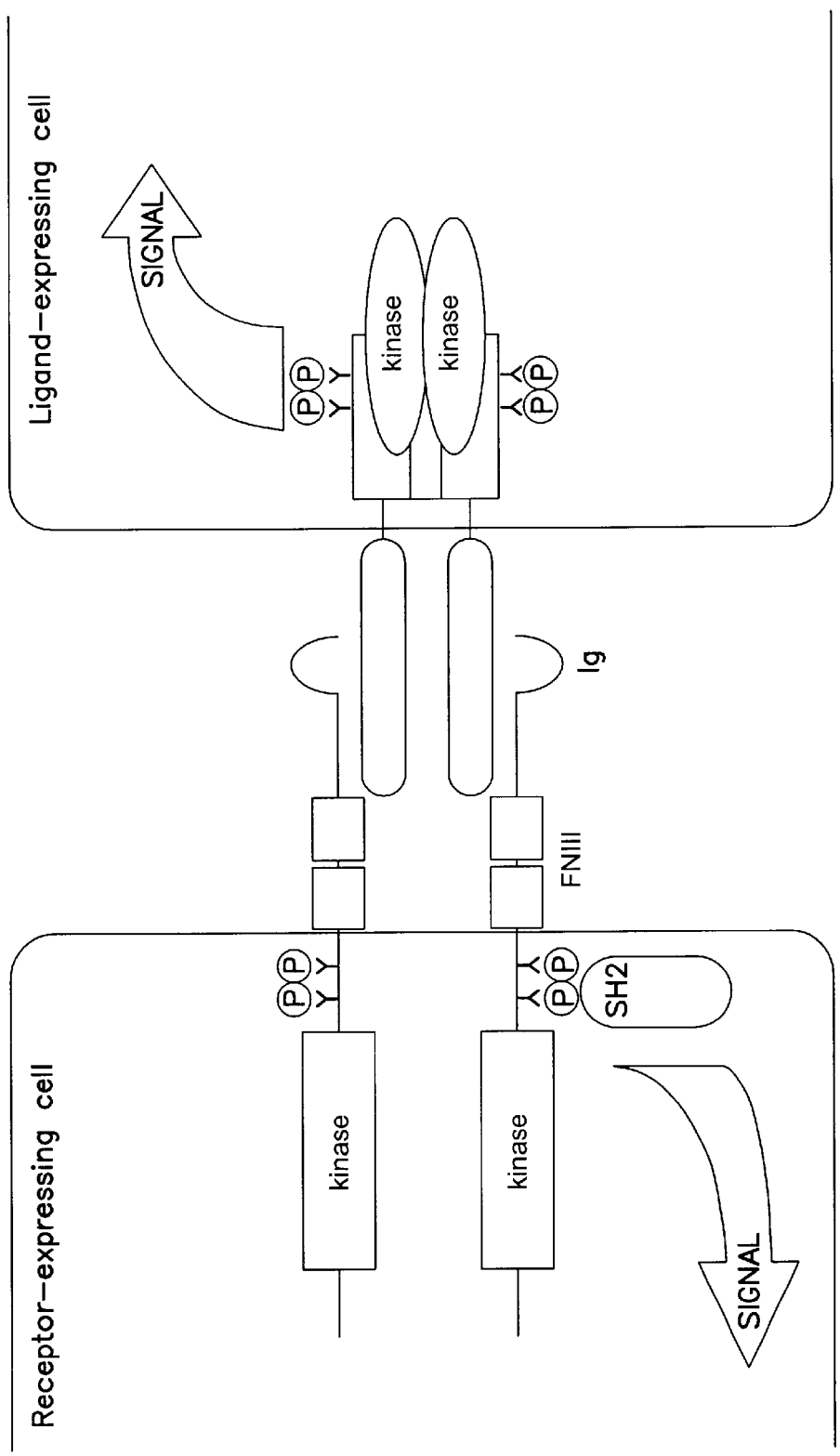
FIG. 4 is a schematic diagram showing bi-directional signalling by Nuk and its TM-ligands.

FIG. 4. Model for bi-directional signalling by Nuk and its TM-ligands. Interaction of the ligand-expressing cell (right) with the receptor-expressing cell (left) promotes aggregation and autophosphorylation of the receptor. This is followed by recruitment of SH2 domain-containing proteins to phosphorylated tyrosines e.g. in the juxtamembrane region[27,28], and tyrosine phosphorylation of cellular proteins. Concomitantly, interaction of the receptor with TM-ligands causes ligand clustering and phosphorylation by an associated tyrosine kinase, leading to propagation of signals in the ligand presenting cell.

Description of Results

Nuk belongs to a subclass of Eph receptors that bind specifically to the TM-subgroup of Eph receptor ligands[11,14,19]. Genetic analysis of Nuk in the mouse has revealed a physiological role for this receptor in pathfinding of specific anterior commissure axons, and has raised the possibility that the TM-ligands might themselves possess a signalling function, which is activated by binding of the Nuk extracellular domain[6]. The three known TM-ligands have highly conserved cytoplasmic domains, and are virtually identical over their C-terminal 33 amino acids[12-17]. These sequences contain five potential tyrosine phosphorylation sites (FIG. 1A). A GST fusion protein containing the cytoplasmic domain of human Elk-L (residues 262–343) was tyrosine phosphorylated by v-Src in vitro (FIG. 1B), whereas GST alone or a fusion protein containing the Elk-L extracellular domain were not (FIG. 1B and data not shown).

To investigate whether full-length Elk-L or Htk-L could be phosphorylated on tyrosine in vivo, these TM-ligands were expressed in Cos-1 cells either alone or in combination with v-Src. The ligands were then precipitated from the transfected cells using either an antibody to the common C-terminal region of Elk-L and Htk-L (anti-ligand) or a fusion protein containing the extracellular domain of Nuk fused to the Fc region of the Ig heavy chain (Nuk-Fc[11]), which binds with high affinity to the extracellular domain of TM-ligands. When such precipitates were blotted with ligand antibody, a diffuse band of approximately 45–48 kDa was specifically detected in cells transfected with Elk-L, whereas a protein of between 38 and 46 kDa was identified in cells transfected with Htk-L (FIG. 1C lower panel). The predicted molecular weights of Elk-L and Htk-L are 38 and 37 kDa respectively, and their slow electrophoretic mobility is apparently due to glycosylation (data not shown). Immunoblotting of anti-ligand immunoprecipitates from transfected Cos-1 cells with antibodies to phosphotyrosine (FIG. 1C upper panel) showed that both Elk-L and Htk-L were basally phosphorylated on tyrosine at low levels. Co-transfection of Elk-L with v-Src led to the appearance of a highly tyrosine phosphorylated ~48 kDa form of Elk-L in both anti-ligand and Nuk-Fc precipitates (FIG. 1C upper panel and FIG. 1D). In addition a tyrosine phosphorylated protein of 130–140 kDa was observed to co-precipitate with Elk-L from cells co-expressing ligand and v-Src. v-Src also induced strong tyrosine phosphorylation of Htk-L, which migrated as a broad band of 38–48 kDa in the phosphorylated form. Immunoprecipitation of both Elk-L/Htk-L and the 130 kDa protein was markedly reduced by addition of the immunizing peptide which competes for antibody binding (data not shown). In v-Src co-transfected cells the total amount of either ligand detected in western blots by the anti-ligand antibodies was reduced. It is possible that these antibodies, which were raised against the C-terminal part of Elk-L, are less efficient in recognising highly tyrosine phosphorylaled forms of the denatured ligands in an immunoblot. These results show that Elk-L and Htk-L are potent in vivo substrates for an activated Src tyrosine kinase, and can be detected in association with other phosphotyrosine-containing proteins in cells expressing both ligand and v-Src.

The phosphorylation of TM-ligands on tyrosine may provide a mechanism by which signals are transmitted into ligand-presenting cells and such a signal might be activated by the clustering of ligands on the cell surface. To address this issue, Cos-1 cells expressing Elk-L or Htk-L were exposed to the Nuk extracellular domain, in the form of a Nuk-Fc fusion protein clustered with anti-Ig. Under these conditions Nuk-Fc induced a several-fold increase in the tyrosine phosphorylation of both Elk-L and Htk-L, whereas no stimulation of ligand tyrosine phosphorylation was induced by Fc alone (FIG. 2A). The tyrosine phosphorylated band immunoprecipitated by the anti-ligand serum was markedly reduced by addition of excess ligand C-terminal peptide to the immunoprecipitates. This experiment indicates that the binding of clustered Nuk-Fc to the TM-ligands induces the activation of an endogenous tyrosine kinase in Cos-1 cells that can subsequently phosphorylate Elk-L and Htk-L. These results, whilst provocative, were performed using exogenously overexpressed ligand. To corroborate these observations in a more physiologically relevant cell type, the human neuroepithelioma cell line CHP-100, previously shown to express endogenous Elk-L[12] was employed. Incubation of CHP-100 cells with clustered Nuk-Fc led to a striking increase in the tyrosine phosphorylation of Elk-L and to coprecipitation of several tyrosine phosphorylated polypeptides (FIG. 2B). Thus, the binding of the Nuk extracellular domain to a cell that normally expresses Elk-L also leads to tyrosine kinase activation and concomitant Elk-L phosphorylation.

These findings raised the possibility that the interaction of a cell expressing TM-ligands on its surface with a second cell expressing Nuk might lead to both the activation of the Nuk receptor, and subsequent signalling within the Nuk-expressing cell, and also to the activation of a ligand-associated kinase and consequent ligand phosphorylation. To test this notion, Cos-1 cells expressing Elk-L or Htk-L were co-cultured with the neuronal cell line NG108-15[20] (NG108), that does not express endogenous Eph receptors which bind TM-ligands, or with a transfected NG108 clone which stably expresses high levels of the 130 kDa mouse Nuk protein (NG108-Nuk). In cocultures of ligand-expressing cells with NG108-Nuk cells, both the induction of Nuk tyrosine phosphorylation, reflecting activation of the Nuk catalytic domain, and also tyrosine phosphorylation of Elk-L or Htk-L, were observed which is consistent with stimulation of a ligand-associated tyrosine kinase in the ligand-expressing cells (FIG. 2C). Parental NG108 cells lacking Nuk were without effect and conversely, no phosphorylation of either TM-ligands or Nuk was induced using untransfected Cos-1 cells (FIG. 2C and data not shown).

The observation that Elk-L and Htk-L are inducibly phosphorylated on tyrosine in cultured cells upon exposure to clustered Nuk-Fc, or Nuk-expressing cells, suggests that this may be a physiological event. To test this possibility, protein lysates from mouse embryos at 10.5 days of development were immunoprecipitated with antibodies to either TM-ligands or Nuk, and the immune complexes were immunoblotted with antibodies to phosphotyrosine (FIG. 3). Nuk immunoprecipitated from embryonic body or head tissue was phosphorylated on tyrosine (FIG. 3 and data not shown). Furthermore, anti-ligand antibodies specifically precipitated phosphotyrosine-containing polypeptides from these embryonic lysates that co-migrated with authentic TM-ligands. The intensity of the tyrosine phosphorylated band immunoprecipitated by the anti-ligand antibodies was markedly reduced by addition of excess ligand C-terminal peptide. These data demonstrate that not only Eph receptors such as Nuk, but also their TM-ligands, are phosphorylated on tyrosine in the developing mouse embryo.

Eph receptors and their ligands are expressed in reciprocal, mutually exclusive domains in the developing embryo[11]. Such expression patterns support data implicating Eph receptors in establishing boundaries between two distinct cell types, for example in the rhombomeres of the hindbrain and in development of the forebrain[9,10]. To achieve this purpose, it would be advantageous if cell-cell contact initiated a bi-directional signal, thereby regulating the phenotype of both receptor- and ligand-expressing cells. The experiments described above demonstrated a biochemical mechanism through which such bi-directional signalling can be achieved (FIG. 4). In the neuronal cell line NG108, activation of Nuk by TM-ligands leads not only to Nuk autophosphorylation, but also the phosphorylation of potential receptor targets (FIG. 2C). The data also indicate that binding of Nuk to TM-ligands activates a tyrosine kinase in the ligand-expressing cell, leading to phosphorylation of the conserved C-terminal region of the ligand itself. The TM-ligands contain several tyrosine residues in a favourable sequence context for phosphorylation by Src-like kinases[21]. One scheme consistent with the results is that phosphorylation of the ligands by Src-like kinases induces the binding of SH2-containing proteins which then transmit signals within the ligand-expressing cell. However, the finding that TM-ligands are highly phosphorylated on tyrosine in mouse embryos suggests that ligand signalling is a significant event in the intact organism.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

Below full citations are set out for the references referred to in the footnotes in the specification.

FULL CITATIONS FOR REFERENCES REFERRED TO IN THE FOOTNOTES IN THE SPECIFICATION

1. Pasquale E. B., Deerinck T. J., Singer S. J., Ellisman M. H. J. Neuroscience 12: 3956–3967 (1992)
2. Henkemeyer M., Marengere L. E. M., McGlade J., Olivier J. P., Conlon R. A., Holmyard D. P.. Letwin K., Pawson T. Oncogene 9: 1001–1014 (1994)
3. Winslow J. W., Moran P., Valverde J., Shih A., Yuan J. G., Wong S. C., Tsai S. P., Goddard A., Henzel W. J., Hefti F., Beck K. D., Caras I. W. Neuron 14: 973–981 (1995)
4. Drescher U., Kremoser C., Handwerker C., Loschinger J., Noda M., Bonhoeffer F. Cell 82: 359–370 (1995)
5. Cheng H-J., Nakamoto M., Bergemann A. D., Flanagan J. G. Cell 82: 371–381 (1995)
6. Henkemeyer M., Orioli D., Henderson J. T., Saxton T. M., Roder J., Pawson T., Klein R. Cell, in press
7. Tessier-Lavigne, M. Cell 82: 345–348 (1995)
8. Pandey A., Shao H., Marks R. M., Polverini P. J., Dixit V. M. Science 268: 587–569 (1995)
9. Xu Q., Alldus G., Holder N., Wilkinson D. G. Development 121: 4005–4016 (1995)
10. Xu Q., Alldus G., Macdonald R., Wilkinson D. G., Holder N. Nature 381: 319–322 (1996)
11. Gale N. W., Holland S. J., Valenzuela D. M., Flenniken A., Pan L., Ryan T. E., Henkemeyer M., Hirai, H., Strebhardt K., Wilkinson D. G., Pawson T., Davis S., Yancopoulos G. D. Neuron, in press
12. Davis S., Gale N. W., Aldrich T. H., Maisonpierre P. C., Lhotak V., Pawson T., Goldfarb, M., Yancopoulos G. D. Science 26: 816–819 (1994)
13. Beckmann M. P., Cerretti D. P., Baum P., Vanden Bos T., James L., Farrah T., Kozlosky, C., Hollingsworth T., Shilling H., Maraskovsky E., Fletcher F. A., Lhotak V., Pawson T., Lyman S. D. EMBO J. 13: 3757–3762 (1994)
14. Shao H., Lou L., Pandey A., Pasquale E. B., Dixit V. M. J. Biol. Chem. 269: 26606–26609 (1994)
15. Bergemann A. D., Cheng H.-J., Brambilla R., Klein R., Flanagan J. G. Mol. Cell Biol. 15: 4921–4929 (1995)
16. Bennett B. D., Zeigler F. C., Gu Q., Fendly B., Goddard A. D., Gillet N., Matthews W. Proc. Natl. Acad. Sci. USA 92: 1886–1870 (1995)
17. Gale N. W., Flenniken A., Compton D. C., Jenkins N., Davis S., Wilkinson D. G., Yancopoulos G. D. Oncogene, in press
18. Taniguchi T. Science 268: 251–255 (1995)
19. Brambilla R., Schnapp A., Casagranda F., Labrador J. P., Bergemann A. D., Flanagan J. G., Pasquale E. B., Klein R. EMBO J. 14: 3116–3126 (1995)
20. Nelson P., Christian C., Nirenberg M. Proc. Nat. Acad. Sci. USA 73: 123–127 (1976)
21. Songyang Z., Carraway K. L. III., Eck M. J., Harrison S. C., Feldman R. A., Mohammadi, M., Schlessinger J., Hubbard S. R, Smith D. P., Eng C., Lorenzo M. J., Ponder B. A. J., Mayer B. J., Cantley L. C. Nature 373: 536–539 (1995)
22. Pandey A., Lindberg R. A., Dixit V. M. Current Biology 5: 986–989 (1995)
23. Stefanova I., Horejsi V., Ansotegui I. J., Knapp W., Stockinger H. Science 254: 1016–1019 (1991)
24. Brown D. Curr. Opin. Immunol. 5: 349–354 (1993)
25. Cerretti D. P.. VandenBos T., Nelson N., Koslosky C. J., Reddy P., Maraskovsky E., Park S., Lyman S. D., Copeland N. G., Gilbert D. J. Mol. Immunol. 32: 1197–1205 (1995)
26. Liu X., Brodeur S. R., Gish G., Songyang Z., Cantley L. C., Laudano A. P., Pawson T., Oncogene 8: 1119–1126 (1993)
27. Lhotak V. and Pawson T. Mol. Cell Biol. 13: 7071–7079 (1993)
28. Ellis C., Kasmi F., Ganju P., Walls E., Panayotou G., Reith A. D. Oncogene 12: 1727–1736 (1996).

We claim:

1. A method for identifying a compound which inhibits or enhances activation of a transmembrane ligand for a receptor tyrosine kinase, selected from Elk-L/LERK2/Efl-3/Cek5-L, hHtk-L/ELF-2/Lerk5, and hElk-L3/Efl-6, in a cell expressing the transmembrane ligand, comprising the steps of:

(a) contacting one of the following:
      (i) a purified and isolated oligomerized receptor tyrosine kinase selected from Nuk, Hek, Erk, Sek3, Cek5, Elk, Cek6a, xEk, Hek2, Sek4, Cek10, Htk and Myk1,
      (ii) a purified and isolated oligomerized isoform of a receptor tyrosine kinase selected from Nuk, Hek, Erk, Sek3, Cek5, Elk, Cek6a, xEk, Hek2, Sek4, Cek10, Htk and Myk1, or
      (iii) a purified and isolated oligomerized extracellular domain of a receptor tyrosine kinase selected from Nuk, Hek, Erk, Sek3, Cek5, Elk, Cek6a, xEk, Hek2, Sek4, Cek10, Htk and Myk1;
      with a cell expressing a transmembrane ligand for a receptor tyrosine kinase selected from Elk-L/LERK2/Efl-3/Cek5-L, hHtk-L/ELF-2/Lerk5, and hElk-L3/Efl-6, which binds to the receptor tyrosine kinase to form receptor-ligand complexes which activate said signal transduction activities of the transmembrane ligand in the cell; and a test compound under conditions which permit the formation of receptor-ligand complexes;
   (b) assaying for activation of the transmembrane ligand;
   (c) performing a control experiment in which said parts (a) and (b) are performed in the absence of said test compound; and
   (d) comparing the effect of said test compound to the effect of the control experiment to determine if said test compound inhibits or enhances activation of the transmembrane ligand in the cell.

2. A method as claimed in claim 1, wherein the transmembrane ligand is Elk-L and the receptor tyrosine kinase is Elk or Nuk.

3. A method as claimed in claim 1, wherein the transmembrane ligand is Htk-L and the receptor tyrosine kinase is Elk or Nuk.

4. A method is claimed in claim 1, wherein the transmembrane ligand comprises the amino acid sequence of SEQ. ID. No. 2, 3, or 4.

5. A method as claimed in claim 1, wherein the receptor tyrosine kinase is Nuk, Elk, Htk, or Hek.

* * * * *

SEQUENCE LISTING

```
<160> NUMBER OF SEQ ID NOS: 13

<210> SEQ ID NO 1
<211> LENGTH: 1120
<212> TYPE: DNA
<213> ORGANISM: Homo sapiens

<400> SEQUENCE: 1 ccgggggtg  ggcgactttg  ggggagttgg  tgccccgccc  cccaggcctt  ggcggggtca      60
tggggccccc  ccattctggg  ccgggggggcg  tgcgagtcgg  ggccctgctg  ctgctggggg    120
ttttggggct  ggtgtctggg  ctcagcctgg  agcctgtcta  ctggaactcg  gcgaataaga    180
ggttccaggc  agagggtggt  tatgtgctgt  accctcagat  cggggaccgg  ctagacctgc    240 tctgccccg   ggcccggcct  cctggccctc  actcctctcc  taattatgag  ttctacaagc    300
tgtacctggt  aggggggtgct  cagggccggc  gctgtgaggc  accccctgcc  ccaaacctcc    360
ttctcacttg  tgatcgccca  gacctggatc  tccgcttcac  catcaagttc  caggagtata    420
gccctaatct  ctggggccac  gagttccgct  cgcaccacga  ttactacatc  attgccacat    480
cggatgggac  ccgggagggc  ctggagagcc  tgcagggagg  tgtgtgccta  accagaggca    540
```

```
tgaaggtgct tctccaagtg ggacaaagtc cccgaggagg ggctgtcccc cgaaaacctg     600
tgtctgaaat gcccatggaa agagaccgag gggcagccca cagcctggag cctgggaagg     660
agaacctgcc aggtgacccc accagcaatg caacctcccg gggtgctgaa ggcccccctgc    720 cccctcccag catgcctgca gtggctgggg cagcaggggg gctggcgctg ctcttgctgg     780
gcgtggcagg ggctgggggt gccatgtgtt ggcggagacg cgggccaag ccttcggaga     840 gtcgccaccc tggtcctggc tccttcggga ggggagggtc tctgggcctg ggggtggag     900 gtgggatggg acctcgggag gctgagcctg ggagctagg gatagctctg cggggtggcg     960
gggctgcaga tccccccttc tgcccccact atgagaaggt gagtggtgac tatgggcatc    1020
ctgtgtatat cgtgcaggat gggcccccc agagccctcc aaacatctac tacaaggtat    1080
gagggctcct ctcacgtggc tatcctgaat ccagcccttc                          1120
```

<210> SEQ ID NO 2
<211> LENGTH: 29
<212> TYPE: DNA
<213> ORGANISM: Rattus norvegicus

<400> SEQUENCE: 2

```
tatcgacttt acgcaccaac aaatggaag                                       29
```

<210> SEQ ID NO 3
<211> LENGTH: 340
<212> TYPE: PRT
<213> ORGANISM: Homo sapiens

<400> SEQUENCE: 3

```
Met Gly Pro Pro His Ser Gly Pro Gly Gly Val Arg Val Gly Ala Leu
 1               5                  10                  15

Leu Leu Leu Gly Val Leu Gly Leu Val Ser Gly Leu Ser Leu Glu Pro
            20                  25                  30

Val Tyr Trp Asn Ser Ala Asn Lys Arg Phe Gln Ala Glu Gly Gly Tyr
        35                  40                  45

Val Leu Tyr Pro Gln Ile Gly Asp Arg Leu Asp Leu Leu Cys Pro Arg
    50                  55                  60

Ala Arg Pro Pro Gly Pro His Ser Ser Pro Asn Tyr Glu Phe Tyr Lys
65                  70                  75                  80

Leu Tyr Leu Val Gly Gly Ala Gln Gly Arg Arg Cys Glu Ala Pro Pro
                85                  90                  95

Ala Pro Asn Leu Leu Leu Thr Cys Asp Arg Pro Asp Leu Asp Leu Arg
            100                 105                 110

Phe Thr Ile Lys Phe Gln Glu Tyr Ser Pro Asn Leu Trp Gly His Glu
        115                 120                 125

Phe Arg Ser His His Asp Tyr Tyr Ile Ile Ala Thr Ser Asp Gly Thr
    130                 135                 140

Arg Glu Gly Leu Glu Ser Leu Gln Gly Gly Val Cys Leu Thr Arg Gly
145                 150                 155                 160

Met Lys Val Leu Leu Gln Val Gly Gln Ser Pro Arg Gly Gly Ala Val
                165                 170                 175

Pro Arg Lys Pro Val Ser Glu Met Pro Met Glu Arg Asp Arg Gly Ala
            180                 185                 190

Ala His Ser Leu Glu Pro Gly Lys Glu Asn Leu Pro Gly Asp Pro Thr
        195                 200                 205

Ser Asn Ala Thr Ser Arg Gly Ala Glu Gly Pro Leu Pro Pro Pro Ser
```

```
              210                 215                 220
Met Pro Ala Val Ala Gly Ala Gly Gly Leu Ala Leu Leu Leu Leu
225                 230                 235                 240

Gly Val Ala Gly Ala Gly Gly Ala Met Cys Trp Arg Arg Arg Ala
                245                 250                 255

Lys Pro Ser Glu Ser Arg His Pro Gly Pro Gly Ser Phe Gly Arg Gly
                260                 265                 270

Gly Ser Leu Gly Leu Gly Gly Gly Gly Met Gly Pro Arg Glu Ala
            275                 280                 285

Glu Pro Gly Glu Leu Gly Ile Ala Leu Arg Gly Gly Ala Ala Asp
        290                 295                 300

Pro Pro Phe Cys Pro His Tyr Glu Lys Val Ser Gly Asp Tyr Gly His
305                 310                 315                 320

Pro Val Tyr Ile Val Gln Asp Gly Pro Pro Gln Ser Pro Asn Ile
                325                 330                 335

Tyr Tyr Lys Val
            340

<210> SEQ ID NO 4
<211> LENGTH: 333
<212> TYPE: PRT
<213> ORGANISM: Homo sapiens

<400> SEQUENCE: 4

Met Ala Val Arg Arg Asp Ser Val Trp Lys Tyr Cys Trp Gly Val Leu
 1               5                  10                  15

Met Val Leu Cys Arg Thr Ala Ile Ser Lys Ser Ile Val Leu Glu Pro
                20                  25                  30

Ile Tyr Met Asn Ser Ser Asn Ser Lys Phe Leu Pro Gly Gln Gly Leu
            35                  40                  45

Val Leu Tyr Pro Gln Ile Gly Asp Lys Leu Asp Ile Ile Cys Pro Lys
        50                  55                  60

Val Asp Ser Lys Thr Val Gly Gln Tyr Glu Tyr Tyr Lys Val Tyr Met
65                  70                  75                  80

Val Asp Lys Asp Gln Ala Asp Arg Cys Thr Ile Lys Lys Glu Asn Thr
                85                  90                  95

Pro Leu Leu Asn Cys Ala Lys Pro Asp Gln Asp Ile Lys Phe Thr Ile
            100                 105                 110

Lys Phe Gln Glu Phe Ser Pro Asn Leu Trp Gly Leu Glu Phe Gln Lys
        115                 120                 125

Asn Lys Asp Tyr Tyr Ile Ile Ser Thr Ser Asn Gly Ser Leu Glu Gly
    130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Pro Asn
                165                 170                 175

Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
        195                 200                 205

Asp Gly Asn Ser Ala Gly His Ser Gly Asn Asn Ile Leu Gly Ser Glu
    210                 215                 220

Val Ala Leu Phe Ala Gly Ile Ala Ser Gly Cys Ile Ile Phe Ile Val
225                 230                 235                 240
```

```
Ile Ile Ile Thr Leu Val Val Leu Leu Lys Tyr Arg Arg His
            245                 250                 255

Arg Lys His Ser Pro Gln His Thr Thr Thr Leu Ser Leu Ser Thr Leu
            260                 265                 270

Ala Thr Pro Lys Arg Ser Gly Asn Asn Asn Gly Ser Glu Pro Ser Asp
            275                 280                 285

Ile Ile Ile Pro Leu Arg Thr Ala Asp Ser Val Phe Cys Pro His Tyr
            290                 295                 300

Glu Lys Val Ser Gly Asp Tyr Gly His Pro Val Tyr Ile Val Gln Glu
305                 310                 315                 320

Met Pro Pro Gln Ser Pro Ala Asn Ile Tyr Tyr Lys Val
            325                 330

<210> SEQ ID NO 5
<211> LENGTH: 345
<212> TYPE: PRT
<213> ORGANISM: Homo sapiens

<400> SEQUENCE: 5

Met Ala Arg Pro Gly Gly Arg Trp Leu Gly Lys Trp Leu Tyr Ala Met
  1               5                  10                  15

Val Val Trp Ala Leu Cys Arg Leu Ala Thr Pro Leu Ala Lys Asn Leu
                 20                  25                  30

Glu Pro Val Ser Trp Ser Ser Leu Asn Pro Lys Phe Leu Ser Gly Lys
             35                  40                  45

Gly Leu Val Ile Tyr Pro Lys Ile Gly Asp Lys Leu Asp Ile Ile Cys
         50                  55                  60

Pro Pro Ala Glu Ala Gly Arg Pro Tyr Glu Tyr Tyr Lys Leu Tyr Leu
 65                  70                  75                  80

Val Arg Pro Glu Gln Ala Ala Ala Cys Ser Thr Val Leu Asp Pro Met
                 85                  90                  95

Val Leu Val Thr Cys Asn Arg Pro Glu Gln Glu Ile Arg Phe Thr Ile
                100                 105                 110

Lys Phe Gln Glu Phe Ser Pro Asn Tyr Met Gly Leu Glu Phe Lys Lys
            115                 120                 125

His His Asp Tyr Tyr Ile Thr Ser Thr Ser Asn Gly Ser Leu Glu Gly
        130                 135                 140

Leu Glu Asn Arg Glu Gly Gly Val Cys Arg Thr Arg Thr Met Lys Ile
145                 150                 155                 160

Ile Met Lys Val Gly Gln Asp Pro Asn Ala Val Thr Pro Glu Gln Leu
                165                 170                 175

Thr Thr Ser Arg Pro Ser Lys Glu Ala Asp Asn Thr Val Lys Met Ala
            180                 185                 190

Thr Gln Ala Pro Gly Ser Arg Gly Ser Leu Gly Asp Ser Asp Gly Lys
        195                 200                 205

His Glu Thr Val Asn Gln Glu Glu Lys Ser Gly Pro Gly Ala Ser Gly
    210                 215                 220

Gly Ser Ser Gly Asp Pro Asp Gly Phe Phe Asn Ser Lys Val Ala Leu
225                 230                 235                 240

Phe Ala Ala Val Gly Ala Gly Cys Val Ile Phe Leu Leu Ile Ile Ile
                245                 250                 255

Phe Leu Thr Val Leu Leu Leu Lys Leu Pro Lys Arg His Arg Lys His
            260                 265                 270

Thr Gln Arg Ala Ala Ala Leu Ser Leu Ser Thr Ile Ala Ser Pro Lys
        275                 280                 285
```

Gly Gly Ser Gly Thr Ala Gly Thr Glu Pro Ser Asp Ile Ile Ile Pro
            290                 295                 300

Leu Phe Thr Thr Glu Asn Asn Tyr Cys Pro His Tyr Glu Lys Val Ser
305                 310                 315                 320

Gly Asp Tyr Gly His Pro Val Tyr Ile Val Gln Glu Met Pro Pro Gln
            325                 330                 335

Ser Pro Ala Asn Ile Tyr Tyr Lys Val
            340                 345

<210> SEQ ID NO 6
<211> LENGTH: 209
<212> TYPE: PRT
<213> ORGANISM: Mus musculus

<400> SEQUENCE: 6

Met Ala Arg Ala Gln Arg Pro Leu Leu Pro Leu Leu Leu Leu Leu Leu
  1               5                  10                  15

Pro Leu Arg Ala Arg Asn Glu Asp Pro Ala Arg Ala Asn Ala Asp Arg
             20                  25                  30

Tyr Ala Val Tyr Trp Asn Arg Ser Asn Pro Arg Phe Gln Val Ser Ala
         35                  40                  45

Val Gly Asp Gly Gly Gly Tyr Thr Val Glu Val Ser Ile Asn Asp Tyr
 50                  55                  60

Leu Asp Ile Tyr Cys Pro His Tyr Gly Ala Pro Leu Pro Pro Ala Glu
65                  70                  75                  80

Arg Met Glu Arg Tyr Ile Leu Tyr Met Val Asn Gly Glu Gly His Ala
                 85                  90                  95

Ser Cys Asp His Arg Gln Arg Gly Phe Lys Arg Trp Glu Cys Asn Arg
            100                 105                 110

Pro Ala Ala Pro Gly Gly Pro Leu Lys Phe Ser Glu Lys Phe Gln Leu
            115                 120                 125

Phe Thr Pro Phe Ser Leu Gly Phe Glu Phe Pro Pro Gly His Glu Tyr
130                 135                 140

Tyr Tyr Ile Ser Ala Thr Pro Pro Asn Leu Val Asp Arg Pro Cys Leu
145                 150                 155                 160

Arg Leu Lys Val Tyr Val Arg Pro Thr Asn Glu Thr Leu Tyr Glu Ala
                165                 170                 175

Pro Glu Pro Ile Phe Thr Ser Asn Ser Ser Cys Ser Gly Leu Gly Ala
            180                 185                 190

Cys His Leu Phe Leu Thr Thr Val Pro Val Leu Trp Ser Leu Leu Gly
            195                 200                 205

Ser

<210> SEQ ID NO 7
<211> LENGTH: 233
<212> TYPE: PRT
<213> ORGANISM: Homo sapiens

<400> SEQUENCE: 7

Met Ala Ala Ala Pro Leu Leu Leu Leu Leu Leu Val Pro Val Pro Pro
  1               5                  10                  15

Leu Leu Pro Leu Leu Ala Gly Gly Pro Ala Gly Ala Leu Gly Asn Arg
             20                  25                  30

His Ala Val Tyr Trp Asn Ser Ser Asn Gln His Leu Arg Arg Glu Gly
         35                  40                  45

```
Tyr Thr Val Gln Val Asn Val Asn Asp Tyr Leu Asp Ile Tyr Cys Pro
     50                  55                  60

His Tyr Asn Ser Ser Gly Ala Gly Pro Gly Pro Gly Gly Gly Ala Glu
 65                  70                  75                  80

Tyr Val Leu Tyr Met Val Ser Arg Asn Gly Tyr Arg Thr Cys Asn Ala
                 85                  90                  95

Ser Gln Gly Phe Lys Arg Trp Glu Cys Asn Arg Pro His Ala Pro His
            100                 105                 110

Ser Pro Ile Lys Phe Ser Glu Lys Phe Gln Arg Tyr Ser Ala Phe Ser
            115                 120                 125

Leu Gly Tyr Glu Phe His Ala Gly His Glu Tyr Tyr Ile Ser Thr
            130                 135                 140

Pro Thr His Asn Leu His Trp Lys Cys Leu Arg Met Lys Val Phe Val
145                 150                 155                 160

Cys Cys Ala Ser Thr Ser His Ser Gly Glu Lys Pro Val Pro Thr Leu
                165                 170                 175

Pro Gln Phe Thr Met Gly Pro Asn Val Lys Ile Asn Val Leu Glu Asp
            180                 185                 190

Phe Glu Gly Glu Asn Pro Gln Val Pro Lys Leu Glu Lys Ser Ile Ser
            195                 200                 205

Gly Thr Ser Pro Lys Arg Glu His Leu Pro Ala Leu Val Gly Ile Ala
            210                 215                 220

Phe Phe Leu Met Thr Phe Leu Ala Ser
225                 230

<210> SEQ ID NO 8
<211> LENGTH: 201
<212> TYPE: PRT
<213> ORGANISM: Homo sapiens

<400> SEQUENCE: 8

Met Arg Leu Leu Pro Leu Leu Ile Thr Val Leu Trp Ala Ala Phe Leu
  1               5                  10                  15

Gly Ser Pro Leu Arg Gly Gly Ser Ser Leu Arg His Val Val Tyr Trp
             20                  25                  30

Asn Ser Ser Asn Pro Arg Ser Leu Arg Gly Asp Ala Val Val Glu Leu
         35                  40                  45

Gly Leu Asn Asp Tyr Leu Asp Ile Val Cys Pro His Tyr Glu Gly Pro
 50                  55                  60

Gly Pro Pro Glu Gly Pro Glu Thr Phe Ala Leu Tyr Met Val Asp Trp
 65                  70                  75                  80

Pro Gly Tyr Glu Ser Cys Gln Ala Glu Gly Pro Arg Gly Tyr Lys Arg
                 85                  90                  95

Trp Val Cys Ser Leu Pro Phe Gly His Val Gln Phe Ser Glu Lys Ile
            100                 105                 110

Gln Arg Phe Thr Pro Phe Ser Leu Gly Phe Glu Phe Leu Pro Gly Glu
            115                 120                 125

Thr Tyr Tyr Tyr Ile Ser Val Pro Thr Pro Glu Ser Ser Gly Gln Cys
            130                 135                 140

Leu Arg Leu Gln Val Ser Val Cys Cys Lys Glu Arg Lys Ser Glu Ser
145                 150                 155                 160

Ala His Pro Val Gly Ser Pro Gly Glu Ser Gly Thr Ser Gly Trp Arg
                165                 170                 175

Gly Gly Asp Thr Pro Ser Pro Leu Cys Leu Leu Leu Leu Leu Leu Leu
            180                 185                 190
```

-continued

```
Leu Ile Leu Arg Leu Leu Arg Ile Leu
        195                 200

<210> SEQ ID NO 9
<211> LENGTH: 228
<212> TYPE: PRT
<213> ORGANISM: Homo sapiens

<400> SEQUENCE: 9

Met Leu His Val Glu Met Leu Thr Leu Val Phe Leu Val Leu Trp Met
  1               5                  10                  15

Cys Val Phe Ser Gln Asp Pro Gly Ser Lys Ala Val Ala Asp Arg Tyr
             20                  25                  30

Ala Val Tyr Trp Asn Ser Ser Asn Pro Arg Phe Gln Arg Gly Asp Tyr
         35                  40                  45

His Ile Asp Val Cys Ile Asn Asp Tyr Leu Asp Val Phe Cys Pro His
     50                  55                  60

Tyr Glu Asp Ser Val Pro Glu Asp Lys Thr Glu Arg Tyr Val Leu Tyr
 65                  70                  75                  80

Met Val Asn Phe Asp Gly Tyr Ser Ala Cys Asp His Thr Ser Lys Gly
                 85                  90                  95

Phe Lys Arg Trp Glu Cys Asn Arg Pro His Ser Pro Asn Gly Pro Leu
            100                 105                 110

Lys Phe Ser Glu Lys Phe Gln Leu Phe Thr Pro Phe Ser Leu Gly Phe
        115                 120                 125

Glu Phe Pro Pro Gly Arg Glu Tyr Phe Tyr Ile Ser Ser Ala Ile Pro
    130                 135                 140

Asp Asn Gly Arg Arg Ser Cys Leu Lys Leu Lys Val Phe Val Arg Pro
145                 150                 155                 160

Thr Asn Ser Cys Met Lys Thr Ile Gly Val His Asp Arg Val Phe Asp
                165                 170                 175

Val Asn Asp Lys Val Glu Asn Ser Leu Glu Pro Ala Asp Asp Thr Val
            180                 185                 190

His Glu Ser Ala Glu Pro Ser Arg Gly Glu Asn Ala Ala Gln Thr Pro
        195                 200                 205

Arg Ile Pro Ser Arg Leu Leu Ala Ile Leu Leu Phe Leu Leu Ala Met
    210                 215                 220

Leu Leu Thr Leu
225

<210> SEQ ID NO 10
<211> LENGTH: 205
<212> TYPE: PRT
<213> ORGANISM: Homo sapiens

<400> SEQUENCE: 10

Met Glu Phe Leu Trp Ala Pro Leu Leu Gly Leu Cys Cys Ser Leu Ala
  1               5                  10                  15

Ala Ala Asp Arg His Thr Val Phe Trp Asn Ser Ser Asn Pro Lys Phe
             20                  25                  30

Arg Asn Glu Asp Tyr Thr Ile His Val Gln Leu Asn Asp Tyr Val Asp
         35                  40                  45

Ile Ile Cys Pro His Tyr Glu Asp His Ser Val Ala Asp Ala Ala Met
     50                  55                  60

Glu Gln Tyr Ile Leu Tyr Leu Val Glu His Glu Glu Tyr Gln Leu Cys
 65                  70                  75                  80
```

```
Gln Pro Gln Ser Lys Asp Gln Val Arg Trp Gln Cys Asn Arg Pro Ser
                 85                  90                  95
Ala Lys His Gly Pro Glu Lys Leu Ser Glu Lys Phe Gln Arg Phe Thr
            100                 105                 110
Pro Phe Thr Leu Gly Lys Glu Phe Lys Glu Gly His Ser Tyr Tyr Tyr
            115                 120                 125
Ile Ser Lys Pro Ile His Gln His Glu Asp Arg Cys Leu Arg Leu Lys
            130                 135                 140
Val Thr Val Ser Gly Lys Ile Thr His Ser Pro Gln Ala His Val Asn
145                 150                 155                 160
Pro Gln Glu Lys Arg Leu Ala Ala Asp Asp Pro Glu Val Arg Val Leu
                165                 170                 175
His Ser Ile Gly His Ser Ala Ala Pro Arg Leu Phe Pro Leu Ala Trp
                180                 185                 190
Thr Val Leu Leu Leu Pro Leu Leu Leu Gln Arg Pro
                195                 200                 205
```

<210> SEQ ID NO 11
<211> LENGTH: 82
<212> TYPE: PRT
<213> ORGANISM: Homo sapiens

<400> SEQUENCE: 11

```
Leu Arg Lys Arg His Arg Lys His Thr Gln Gln Arg Ala Ala Ala Leu
  1               5                  10                  15
Ser Leu Ser Thr Leu Ala Ser Pro Lys Gly Gly Ser Gly Thr Ala Gly
                 20                  25                  30
Thr Glu Pro Ser Asp Ile Ile Ile Pro Leu Arg Thr Thr Glu Asn Asn
                 35                  40                  45
Tyr Cys Pro His Tyr Glu Lys Val Ser Gly Asp Tyr Gly His Pro Val
             50                  55                  60
Tyr Ile Val Gln Glu Met Pro Pro Gln Ser Pro Ala Asn Ile Tyr Tyr
 65                  70                  75                  80
Lys Val
```

<210> SEQ ID NO 12
<211> LENGTH: 82
<212> TYPE: PRT
<213> ORGANISM: Homo sapiens

<400> SEQUENCE: 12

```
Tyr Arg Arg Arg His Arg Lys His Ser Pro Gln His Thr Thr Thr Leu
  1               5                  10                  15
Ser Leu Ser Thr Leu Ala Thr Pro Lys Arg Ser Gly Asn Asn Asn Gly
                 20                  25                  30
Ser Glu Pro Ser Asp Ile Ile Ile Pro Leu Arg Thr Ala Asp Ser Val
                 35                  40                  45
Phe Cys Pro His Tyr Glu Lys Val Ser Gly Asp Tyr Gly His Pro Val
             50                  55                  60
Tyr Ile Val Gln Glu Met Pro Pro Gln Ser Pro Ala Asn Ile Tyr Tyr
 65                  70                  75                  80
Lys Val
```

<210> SEQ ID NO 13
<211> LENGTH: 89
<212> TYPE: PRT

```
<213> ORGANISM: Homo sapiens

<400> SEQUENCE: 13

Arg Arg Arg Arg Ala Lys Pro Ser Glu Ser Arg His Pro Gly Pro Gly
  1               5                  10                  15

Ser Phe Gly Arg Gly Gly Ser Leu Gly Leu Gly Gly Gly Gly Gly Met
             20                  25                  30

Gly Pro Arg Glu Ala Glu Pro Gly Glu Leu Gly Ile Ala Leu Arg Gly
             35                  40                  45

Gly Gly Ala Ala Asp Pro Pro Phe Cys Pro His Tyr Glu Lys Val Ser
         50                  55                  60

Gly Asp Tyr Gly His Pro Val Tyr Ile Val Gln Asp Gly Pro Pro Gln
 65                  70                  75                  80

Ser Pro Pro Asn Ile Tyr Tyr Lys Val
                 85
```